United States Patent
Miwa

(10) Patent No.: US 10,544,160 B2
(45) Date of Patent: Jan. 28, 2020

(54) PRODUCTION METHOD OF THIENOPYRIMIDINE DERIVATIVE

(71) Applicant: Takeda Pharmaceutical Company Limited, Osaka (JP)

(72) Inventor: Kazuhiro Miwa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/116,804

(22) Filed: Aug. 29, 2018

(65) Prior Publication Data

US 2019/0055261 A1    Feb. 21, 2019

Related U.S. Application Data

(62) Division of application No. 15/481,505, filed on Apr. 7, 2017, now Pat. No. 10,150,778, which is a division of application No. 14/432,188, filed as application No. PCT/JP2013/077013 on Sep. 27, 2013, now Pat. No. 9,758,528.

(30) Foreign Application Priority Data

Sep. 28, 2012 (JP) .................. 2012-217679

(51) Int. Cl.
| | | |
|---|---|---|
| *C07D 495/04* | (2006.01) | |
| *C07D 333/38* | (2006.01) | |
| *C07D 409/12* | (2006.01) | |

(52) U.S. Cl.
CPC ......... *C07D 495/04* (2013.01); *C07D 333/38* (2013.01); *C07D 409/12* (2013.01)

(58) Field of Classification Search
CPC .................................................. C07D 495/04
See application file for complete search history.

(56) References Cited

U.S. PATENT DOCUMENTS

| | | | |
|---|---|---|---|
| 5,312,958 A | 5/1994 | Suenaga et al. | |
| 6,297,379 B1 | 10/2001 | Furuya et al. | |
| 6,340,686 B1 | 1/2002 | Furuya et al. | |
| 7,300,935 B2 | 11/2007 | Cho et al. | |
| 7,569,570 B2 | 8/2009 | Furuya et al. | |
| 8,058,280 B2 * | 11/2011 | Cho .................... | C07D 495/04 514/260.1 |
| 8,735,401 B2 | 5/2014 | Cho et al. | |
| 9,346,822 B2 | 5/2016 | Cho et al. | |
| 9,758,528 B2 | 9/2017 | Fukuoka et al. | |
| 10,150,778 B2 | 12/2018 | Miwa | |
| 10,350,170 B2 | 7/2019 | Yamane et al. | |
| 2003/0055269 A1 | 3/2003 | Fukuoka et al. | |
| 2009/0048273 A1 | 2/2009 | Furuya et al. | |
| 2011/0172249 A1 | 7/2011 | Kamikawa et al. | |
| 2017/0210753 A1 | 7/2017 | Fukuoka et al. | |
| 2018/0036250 A1 | 2/2018 | Yamane et al. | |
| 2018/0319816 A1 | 11/2018 | Miwa et al. | |

FOREIGN PATENT DOCUMENTS

| | | |
|---|---|---|
| EP | 1 266 898 A1 | 12/2002 |
| EP | 1 591 446 A1 | 11/2005 |
| JP | H-06-192170 A | 7/1994 |
| JP | H-10-298156 A | 11/1998 |
| JP | 2001-278884 A | 10/2001 |
| JP | 2001-316391 A | 11/2001 |
| JP | 2002-068044 A | 3/2002 |
| WO | WO-00/56739 A1 | 9/2000 |
| WO | WO-2004/067535 A1 | 8/2004 |
| WO | WO-20141051164 A2 | 4/2014 |
| WO | WO-20141051164 A3 | 4/2014 |

OTHER PUBLICATIONS

Chinese office action dated Nov. 17, 2016, for Chinese patent application No. 201380051107.2, 14 pages (with English translation).
Ex Parte Quayle Action mailed on Jun. 5, 2018, for U.S. Appl. No. 15/481,505, filed Apr. 7, 2017, 4 pages.
International Search Report dated Mar. 24, 2014, for PCT Application No. PCT/JP2013/077013, filed on Sep. 27, 2013, 7 pages.
Miwa, K. et al. (2011). "Discovery of 1-{4-[1-(2,6-difluorobenzyl)-5-[(dimethylamino)methyl]-3-(6-methoxypyridazin-3-yl)-2,4-dioxo-1,2,3,4-tetrahydrothieno[2,3-d]pyrimidin-6-yl]phenyl)-3-methoxyurea (TAK-385) as a potent, orally active, non-peptide antagonist of the human gonadotropin-releasing hormone receptor," *J. Med. Chem.* 54:4998-5012.
Non-Final Office Action dated May 12, 2016, for U.S. Appl. No. 14/432,188, filed Mar. 27, 2015, 4 pages.
Non-Final Office Action dated Nov. 21, 2017, for U.S. Appl. No. 15/481,505, filed Apr. 7, 2017, 7 pages.
Notice of Allowance dated May 17, 2017, for U.S. Appl. No. 14/432,188, filed Mar. 27, 2015, 5 pages.
Notice of Allowance dated Sep. 17, 2018, for U.S. Appl. No. 15/481,505, filed Apr. 7, 2017, 5 pages.
Written Opinion of the International Searching Authority dated Mar. 24, 2014, for PCT Application No. PCT/JP2013/077013, filed on Sep. 27, 2013, 10 pages.
Non-Final Office Action dated Mar. 22, 2019, for U.S. Appl. No. 16/034,002, filed Jul. 12, 2018, 4 pages.

(Continued)

*Primary Examiner* — Paul V Ward

(74) *Attorney, Agent, or Firm* — Cooley LLP

(57) ABSTRACT

The present invention provides a production method of a thienopyrimidine derivative or a salt thereof which has a gonadotropin releasing hormone (GnRH) antagonistic action with high quality in high yield. The present invention provides a method of producing a thienopyrimidine derivative, which comprises reacting 6-(4-aminophenyl)-1-(2,6-difluorobenzyl)-5-dimethylaminomethyl-3-(6-methoxy-pyridazin-3-yl)thieno[2,3-d]pyrimidine-2,4(1H,3H)-dione or salt thereof, 1,1'-carbonyldiimidazole or a salt thereof and methoxyamine or a salt thereof, and the like.

3 Claims, 2 Drawing Sheets

(56) References Cited

OTHER PUBLICATIONS

Caira, M.R. (1998). "Crystalline polymorphism of organic compounds," Topics in Curr. Chem. 198:163-208.
Extended European Search Report dated Nov. 9, 2018, for EP Application No. 18 185 835.8, flied on Sep. 27, 2013, 5 pages.
Notice of Allowance dated Jul. 3, 2019, for U.S. Appl. No. 16/034,002, filed Jul. 12, 2018, 5 pages.

* cited by examiner

PRODUCTION METHOD OF THIENOPYRIMIDINE DERIVATIVE

CROSS-REFERENCE TO RELATED APPLICATIONS

This application is a divisional application of U.S. application Ser. No. 15/481,505, filed on Apr. 7, 2017, which is a divisional application of U.S. application Ser. No. 14/432,188, filed on Mar. 27, 2015, now issued as U.S. Pat. No. 9,758,528, which is a U.S. National Stage Application under 35 U.S.C. § 371 of International Application No. PCT/JP2013/077013, filed on Sep. 27, 2013, which claims priority to Japanese Application No. 2012/217679, filed on Sep. 28, 2012, the subject matter of each of which are herein incorporated by reference in their entireties.

TECHNICAL FIELD

The present invention relates to a production method of a thienopyrimidine derivative having a gonadotropin releasing hormone (GnRH) antagonistic action.

BACKGROUND OF THE INVENTION

Secretion of anterior pituitary hormones undergoes feedback control by peripheral hormones secreted from target organs of the respective hormones and by secretion-regulating hormones from the hypothalamus, which is the upper central organ of the anterior lobe of the pituitary (hereinafter, these hormones are collectively called "hypothalamic hormones" in this specification). Presently, as hypothalamic hormones, the existence of nine kinds of hormones including, for example, thyrotropin releasing hormone (TRH), and gonadotropin releasing hormone [GnRH, sometimes called as LH-RH (luteinizing hormone releasing hormone)] has been confirmed. By preventing LH-RH from binding with the LH-RH receptor in the anterior pituitary gland and suppressing the secretion of luteinizing hormone (LH) and follicle stimulation hormone (FSH) from the anterior pituitary gland, an antagonist for gonadotropin releasing hormone controls the effect of LH and FSH on the ovary, reduces the level of estrogen in blood, which is known to be associated with the development of endometriosis and uterine fibroids, and is expected to improve the symptoms of these disorders.

As thienopyrimidine derivatives having gonadotropin releasing hormone and production methods thereof, for example, those described in Patent Document 1 and 2 and Non-Patent Document 1 are known.

DOCUMENT LIST

Patent Document

Patent Document 1: WO 00/56739
Patent Document 2: WO 2004/067535

Non-Patent Document

Non-Patent Document 1: J. Med. Chem., 2011, vol. 54, pages 4998-5012

SUMMARY OF THE INVENTION

Problems to be Solved by the Invention

There is a demand for the development of a safe production method of a thienopyrimidine derivative or a salt thereof which has a gonadotropin releasing hormone antagonistic action with high quality (e.g., high purity) in high yield.

Means of Solving the Problems

The present inventors have conducted intensive studies in an attempt to solve the above-mentioned problem and found that, by employing the production method of the present invention, 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof with high quality can be more safely obtained in high yield, which resulted in the completion of the present invention.

Accordingly, the present invention relates to

[1] a method of producing 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-3 methoxyurea or a salt thereof, which comprises reacting 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione or salt thereof, 1,1'-carbonyldiimidazole or a salt thereof and methoxyamine or a salt thereof;

[2] the method of the above-mentioned [1], wherein the 1,1'-carbonyldiimidazole or a salt thereof is used in an amount of 1.6 to 2.5 equivalents relative to 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione or a salt thereof, and the methoxyarmine or a salt thereof is used in an amount of 1.0 to 1.5 equivalents relative to 1,1'-carbonyldiimidazole or a salt thereof;

[2A] a method of producing a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof, which comprises reacting 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione or salt thereof, 1,1'-carbonyldiimidazole or a salt thereof and methoxyamine or a salt thereof, and adding tetrahydrofuran to the resulting reaction mixture (may be a reaction solution) or 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof isolated from the resulting reaction mixture (may be a reaction solution);

[3] a method of producing a crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof, which comprises recrystallizing a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof using an alkyl alcohol and one solvent selected from the group consisting of dimethylsulfoxide, dimethylformamide (N,N'-dimethylformamide, in the present specification, to also be referred to as DMF) and dimethylacetamide (N,N'-dimethylacetamide, in the present specification, to also be referred to as DMAc);

[4] a method of producing ethyl (2,6-difluorobenzyl)-[4-dimethylaminomethyl-3-(6-methoxypyridazin-3-ylcarbamoyl)-5-(4-nitrophenyl)thiophen-2-yl]carbamate or a salt thereof, which comprises reacting 2-[(2,6-difluorobenzyl)ethoxycarbonylamino]-4-dimethylaminomethyl-5-(4-nitrophenyl)thiophene-3-carboxylic acid or a salt thereof with 3-amino-6-methoxypyridazine or a salt thereof in the presence of propylphosphonic anhydride and a base;

[5] a method of producing 1-{4-[1-(2,6-difluorobenzyl)-5-dimethylaminomethyl-3-(6-ethoxypyridazin-3-yl)-2,4-dioxo-1,2,3,4-tetrahydrothieno[2,3-d]pyrimidin-6-yl]phenyl}-3-methoxyurea or a salt thereof, which comprises reacting 2-[(2,6-difluorobenzyl)ethoxycarbonylamino]-4-dimethylaminomethyl-5-(4-nitrophenyl)thiophene-3-carboxylic acid or a salt thereof with 3-amino-6-methoxypyridazine or a salt thereof in the presence of propylphosphonic anhydride and a base, subjecting the obtained ethyl (2,6-difluorobenzyl)-[4-dimethylaminomethyl-3-(6-methoxypyridazin-3-ylcarbamoyl)-5-(4-nitrophenyl)thiophen-2-yl]carbamate or a salt thereof to a cyclization reaction, subjecting the obtained 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione or a salt thereof to a reduction reaction, and reacting the obtained 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione or a salt thereof, 1,1'-carbonyldiimidazole or a salt thereof and methoxyamine or a salt thereof;

[6] a method of producing ethyl 4-bromomethyl-2-[(2,6-difluorobenzyl)ethoxycarbonylamino]-5-(4-nitrophenyl)thiophene-3-carboxylate or a salt thereof, which comprises reacting ethyl 2-[(2,6-difluorobenzyl)ethoxycarbonylamino]-4-methyl-5-(4-nitrophenyl)thiophene-3-carboxylate or a salt thereof with N-bromnosuccinimide in the presence of 2,2'-azobis(2,4-dimethylvaleronitrile) and trifluoromethylbenzene;

[7] a method of producing 1-{4-[1-(2,6-difluorobenzyl)-5-dimethylamninomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof, which comprises reacting ethyl 2-[(2,6-difluorobenzyl)ethoxycarbonylamino]-4-methyl-5-(4-nitrophenyl)thiophene-3-carboxylate or a salt thereof with N-bromosuccinimide in the presence of 2,2'-azobis(2,4-dimethylvaleronitrile) and trifluoromethylbenzene, reacting the obtained ethyl 4-bromomethyl-2-[(2,6-difluorobenzyl)ethoxycarbonylamino]-5-(4-nitrophenyl)thiophene-3-carboxylate or a salt thereof with dimethylamine or a salt thereof, subjecting the obtained ethyl 2-[(2,6-difluorobenzyl)ethoxycarbonylamino]-4-dimethylaminomethyl-5-(4-nitrophenyl)thiophene-3-carboxylate to hydrolysis, reacting the obtained 2-[(2,6-difluorobenzyl)ethoxycarbonylamino]-4-dimethylaminomethyl-5-(4-nitrophenyl)thiophene-3-carboxylic acid or a salt thereof with 3-amino-6-methoxypyridazine or a salt thereof in the presence of propylphosphonic anhydride and a base, subjecting the obtained ethyl (2,6-difluorobenzyl)-[4-dimethylaminomethyl-3-(6-methoxypyridazin-3-ylcarbamoyl)-5-(4-nitrophenyl)thiophen-2-yl]carbamate or a salt thereof to a cyclization reaction, subjecting the obtained 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione or a salt thereof to a reduction reaction, and reacting the obtained 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione or a salt thereof, 1,1'-carbonyldiimidazole or a salt thereof and methoxyamine or a salt thereof;

[8] a compound represented by the formula (I):

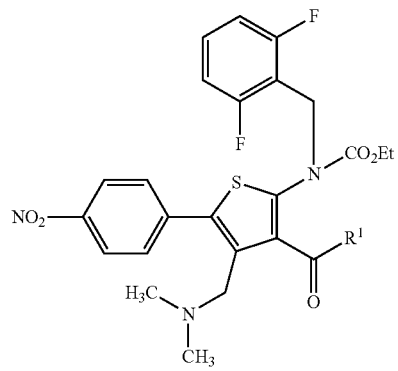

(I)

wherein $R^1$ is a hydroxy group, a $C_{1-6}$ alkoxy group or a $C_{1-6}$ alkoxy-pyridazinylamino group, or a salt thereof (in the present specification, to also be referred to as compound (I));

[9] a compound represented by the formula (II):

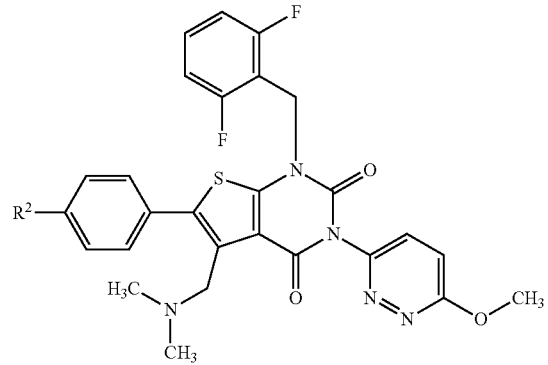

(II)

wherein $R^2$ is a nitro group or an amino group,
or a salt thereof (in the present specification, to also be referred to as compound (II)).

Effect of the Invention

According to the present invention, 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof with high quality can be more safely produced in high yield. In addition, a crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof with high quality can be easily and efficiently produced.

Compounds (I) and (II) are useful as raw material compounds for producing 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof.

DETAILED DESCRIPTION OF THE INVENTION

Figure 1:
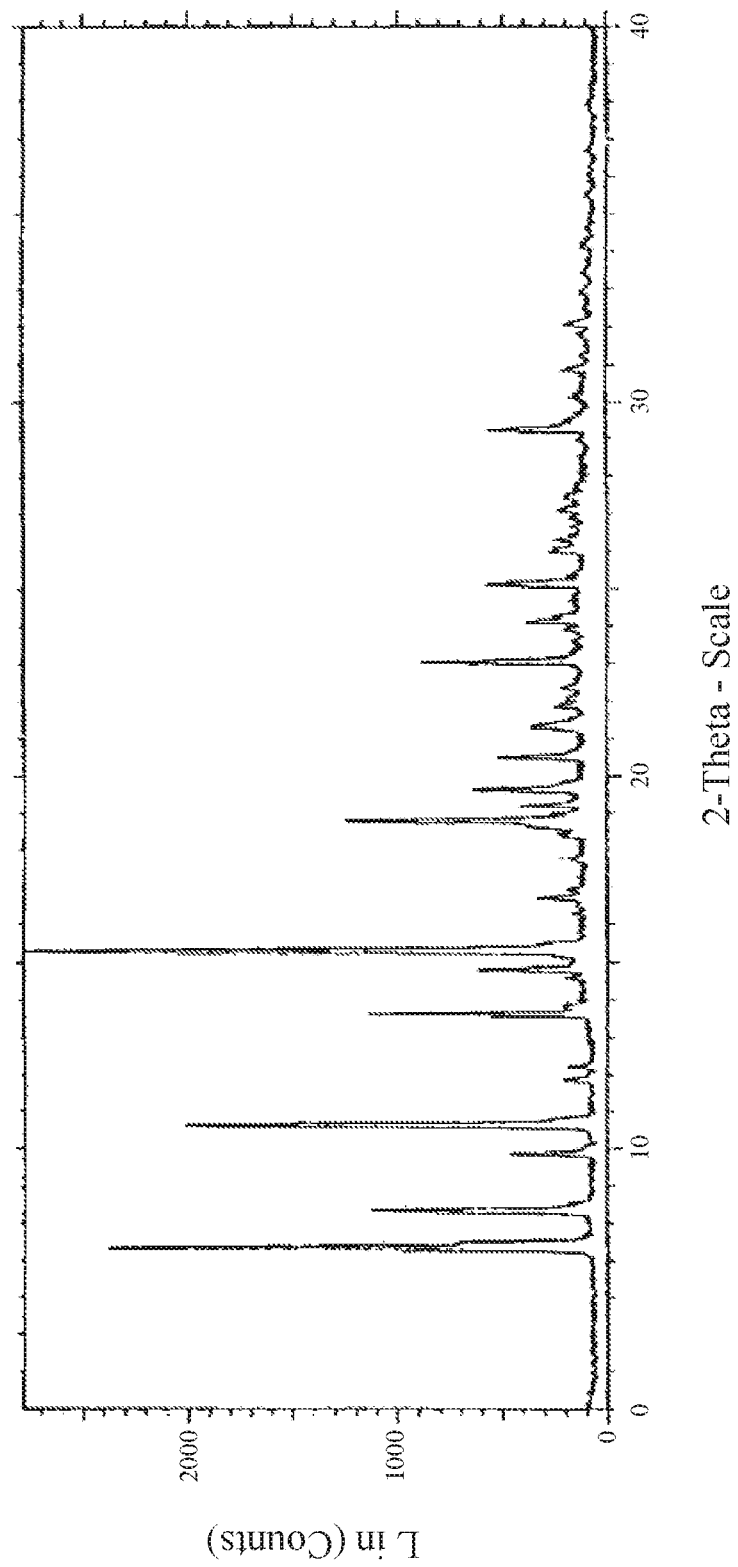
FIG. 1 shows a powder X-ray diffraction pattern of a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea.

The definitions of the terms used in the present invention are explained in detail in the following.

In the present specification, "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like. The $C_{1-6}$ alkoxy group for $R^1$ is preferably ethoxy.

The "$C_{1-6}$ alkoxy-pyridazinylamino group" for $R^1$ means a pyridazinylamino group substituted by 1 to 3 (preferably 1) $C_{1-6}$ alkoxy group(s). The "$C_{1-6}$ alkoxy-pyridazinylamino group" for $R^1$ is preferably a 6-$C_{1-6}$ alkoxy-3-pyridazinylamino group, particularly preferably a 6-methoxy-3-pyridazinylamino group.

The "1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea" in the present specification is identical to N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea described in Patent Document 2.

Next, the production method of the present invention is explained.

Hereinafter, the "room temperature" generally means 1-30° C.

In the following reaction, the raw material compounds, production intermediates and objective compounds may be in the form of a salt. Examples of such salt and salts of compound (I) and compound (II) include a salt with an inorganic acid, a salt with an organic acid, and a salt with an acidic amino acid. Preferable examples of the salt with an inorganic acid include a salt with hydrochloric acid, hydrobromic acid, nitric acid, sulfuric acid or phosphoric acid. Preferable examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid. Preferable examples of the salt with an acidic amino acid include a salt with asparagine acid or glutamic acid. Among them, pharmaceutically acceptable salts are preferably.

The obtained compound in each step can be used directly for the next reaction as the reaction mixture or as a crude product, or can also be isolated according to a conventional method from the reaction mixture, and can also be easily purified according to a separation means (e.g., recrystallization, distillation, chromatography etc.). When the compound in the reaction scheme is a commercially available product, it can also be used directly.

Step 1

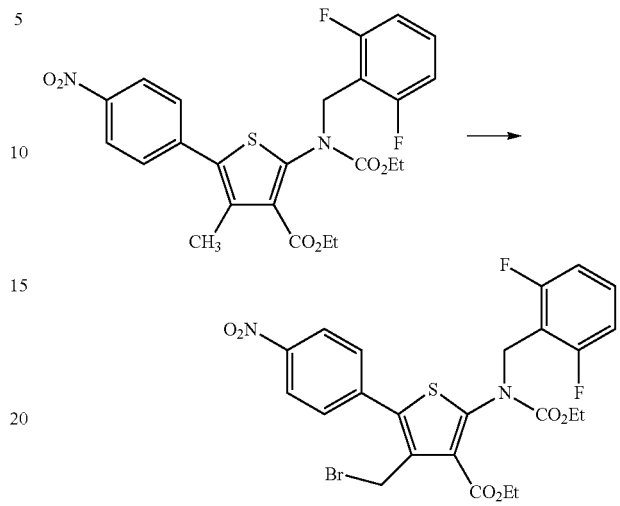

Ethyl 4-bromomethyl-2-[(2,6-difluorobenzyl)ethoxycarbonylamino]-5-(4-nitrophenyl)thiophene-3-carboxylate or a salt thereof (hereinafter to also be referred to as BNTC) can be produced by reacting ethyl 2-[(2,6-difluorobenzyl)ethoxycarbonylamino]-4-methyl-5-(4-nitrophenyl)thiophene-3-carboxylate or a salt thereof (hereinafter to also be referred to as FNTC) with N-bromosuccinimide in the presence of 2,2'-azobis(2,4-dimethylvaleronitrile) and trifluoromethylbenzene. This reaction can also be carried out in a solvent.

The amount of the N-bromosuccinimide to be used is generally 1.0-1.5 equivalents, preferably 1.1-1.4 equivalents, more preferably 1.2-1.3 equivalents, relative to FNTC.

The amount of the 2,2'-azobis(2,4-dimethylvaleronitrile) to be used is generally 0.01-0.2 equivalents, preferably 0.05-0.15 equivalents, relative to FNTC.

The amount of the trifluoromethylbenzene to be used is generally 0.1-1.0 mL, preferably 0.2-0.6 mL, per 1 mmol of FNTC.

The solvent is not particularly limited as long as the reaction proceeds. Examples thereof include ethyl acetate, carbon tetrachloride, dichloromethane, dichloroethane, chlorobenzene, acetonitrile and the like. The solvent is preferably ethyl acetate. In addition, trifluoromethylbenzene or a mixed solvent of trifluoromethylbenzene and an ester (e.g., ethyl acetate etc.) can also be used as a solvent. In the case of the mixed solvent, the ratio (volume ratio) of trifluoromethylbenzene:an ester (e.g., ethyl acetate etc.) in the mixed solvent is preferably 1:0-1:50, more preferably 1:3-1:30.

The reaction temperature is generally 50-80° C., preferably 60-80° C., more preferably 65-75° C.

The reaction time is generally 0.1-5 hr, preferably 0.5-1 hr.

In this step, by using, as a radical initiator, 2,2'-azobis(2,4-dimethylvaleronitrile) having lower toxicity than 2,2'-azobisisobutyronitrile, the bromination reaction can be safely carried out as compared with the reaction described in Patent Document 1 or Non-Patent Document 1. In addition, by using, as a solvent, trifluoromethylbenzene and an ester (e.g., ethyl acetate etc.) having lower toxicity, the bromination reaction can be rapidly carried out as compared with the reaction described in Patent Document 1 or Non-Patent Document 1, and therefore, the production of the impurities can be suppressed.

In another embodiment, the reaction can also be carried out in the absence of trifluoromethylbenzene. Even when carried out in the absence of trifluoromethylbenzene, and BNTC can be produced as according to the method described above or a method analogous thereto.

FNTC can be produced according to the method described in Patent Document 1 or a method analogous thereto.

Step 2

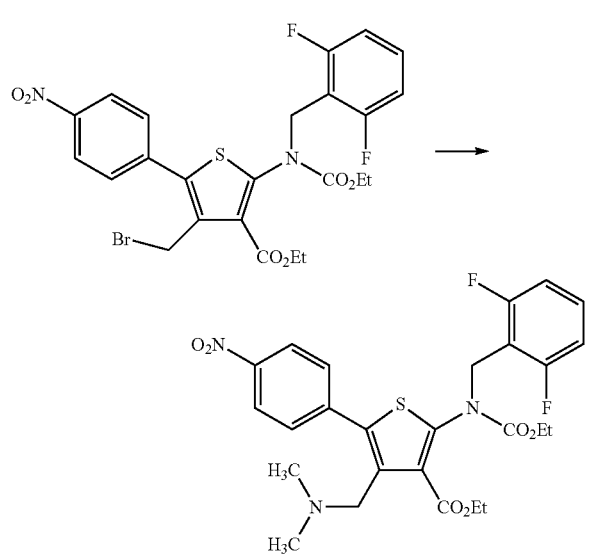

Ethyl 2-[(2,6-difluorobenzyl)ethoxycarbonylamino]-4-dimethylaminomethyl-5-(4-nitrophenyl)thiophene-3-carboxylate or a salt thereof (hereinafter to also be referred to as ANTC) can be produced by reacting BNTC with dimethylamine or a salt thereof. This reaction can also be carried out in a solvent. ANTC is compound (I) wherein $R^1$ is ethoxy.

The amount of the dimethylamine or a salt thereof (preferably dimethylamine hydrochloride) to be used is generally 1.0-3.0 equivalents, preferably 1.2-1.8 equivalents, relative to BNTC.

A base may be used for preferred progress of the reaction. Examples of the base include triethylamine, diisopropylethylamine and the like. The amount of the base to be used is generally 1.0-5.0 equivalents, preferably 2.0-3.0 equivalents, relative to BNTC.

The solvent is not particularly limited as long as the reaction proceeds. Examples thereof include dimethylformamide (DMF), dimethylacetamide (DMAc), tetrahydrofuran and the like. The solvent is preferably DMF. The amount of the solvent to be used is generally 0.5-10 mL, preferably 2.0-4.0 mL, per 1 mmol of BNTC.

The reaction temperature is generally 0-30° C., preferably 10-20° C.

The reaction time is generally 0.5-24 hr, preferably 1-2 hr.

Compound (I) wherein $R^1$ is a $C_{1-6}$ alkoxy group can be produced according to the method described in Step 2 or a method analogous thereto.

Step 3

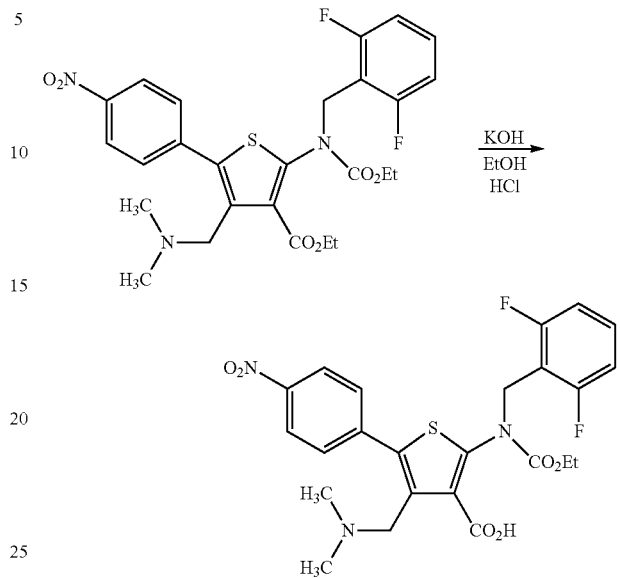

2-[(2,6-Difluorobenzyl)ethoxycarbonylamino]-4-dimethylaminomethyl-5-(4-nitrophenyl)thiophene-3-carboxylic acid or a salt thereof (hereinafter to also be referred to as NTCA) can be produced by subjecting ANTC to hydrolysis. This reaction can also be carried out in a solvent. ANTC is compound (I) wherein $R^1$ is ethoxy. NTCA is compound (I) wherein $R^1$ is a hydroxy group.

The hydrolysis is carried out using a base. The base is not particularly limited, and a base known per se can be used. Examples of the base include potassium hydroxide, sodium hydroxide, lithium hydroxide. Among them, potassium hydroxide is preferable. The amount of the base to be used is generally 1-2 equivalents, preferably 1.2-1.8 equivalents, relative to ANTC.

The hydrolysis is generally carried out in a water-soluble organic solvent. The water-soluble organic solvent is not particularly limited as long as the reaction proceeds. Examples thereof include ethanol, methanol, tetrahydrofuran and the like. The amount of the solvent to be used is generally 1-10 mL, preferably 4-6 mL, per 1 mmol of ANTC.

The reaction temperature is generally 0-80° C., preferably 55-65° C.

The reaction time is generally 1-24 hr, preferably 3-6 hr.

Compound (I) wherein $R^1$ is a $C_{1-6}$ alkoxy group can be produced according to the method described in Step 2 or a method analogous thereto.

Step 4

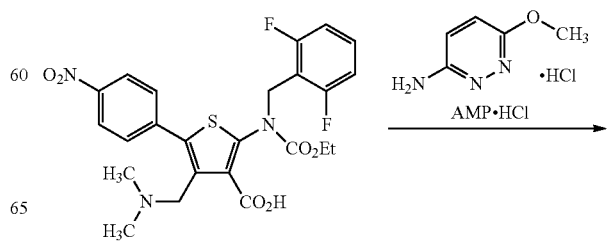

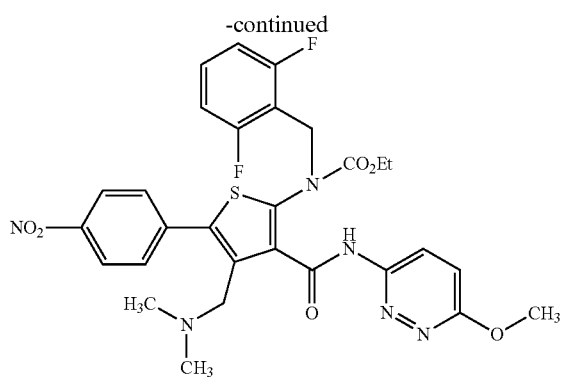

Ethyl (2,6-difluorobenzyl)-[4-dimethylaminomethyl-3-(6-methoxypyridazin-3-ylcarbamoyl)-5-(4-nitrophenyl)thiophen-2-yl]carbamate or a salt thereof (hereinafter to also be referred to as NNTC) can be produced by reacting NTCA with 3-amino-6-methoxypyridazine or a salt thereof (preferably 3-amino-6-methoxypyridazine hydrochloride) in the presence of propylphosphonic anhydride and a base. This reaction can also be carried out in a solvent.

NTCA is compound (I) wherein $R^1$ is a hydroxy group. NNTC is compound (I) wherein $R^1$ is a 6-methoxy-3-pyridazinylamino group.

The amount of the 3-amino-6-methoxypyridazine or a salt thereof to be used is generally 1.0-3.0 equivalents, preferably 1.1-1.5 equivalents, relative to NTCA.

The amount of the propylphosphonic anhydride to be used is generally 1.0-3.0 equivalents, preferably 1.1-1.5 equivalents, relative to NTCA.

Examples of the base include diisopropylethylamine, triethylamine and the like. The amount of the base to be used is generally 1-4 equivalents, preferably 2-3 equivalents, relative to NTCA.

The solvent is not particularly limited as long as the reaction proceeds. Examples thereof include dimethylacetamide (DMAc), dimethylformamide, dimethylsulfoxide, tetrahydrofuran, acetonitrile, ethyl acetate and the like. The amount of the solvent to be used is generally 1-10 mL, preferably 2-4 mL, per 1 mmol of NTCA.

The reaction temperature is generally 0-80° C., preferably 50-60° C.

The reaction time is generally 1-24 hr, preferably 1-3 hr.

Compound (I) wherein $R^1$ is a $C_{1-6}$ alkoxy-pyridazinyl group can be produced according to the method described in Step 4 or a method analogous thereto.

3-Amino-6-methoxypyridazine or a salt thereof (hereinafter to also be referred to as AMP) may be used a commercially available product, or can also be produced, for example, according to the following method.

Step 4'

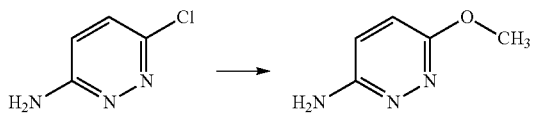

AMP can be produced by reacting 3-amino-6-chloropyridazine (hereinafter to also be referred to as ACP) with sodium methoxide. This reaction can also be carried out in a solvent.

The amount of the sodium methoxide to be used is generally 1.0-2.5 equivalents, preferably 1.1-1.5 equivalents, relative to ACP.

The solvent is not particularly limited as long as the reaction proceeds. Examples thereof include methanol, ethanol, toluene and the like. The amount of the solvent to be used is generally 0.1-10 mL, preferably 0.5-1 mL, per 1 mmol of ACP.

The reaction can also be carried out under high pressure. The internal pressure of the reaction container is generally 0.6-0.9 MPa, preferably 0.65-0.75 MPa.

The reaction temperature is generally 110-140° C., preferably 120-135° C.

The reaction time is generally 6-24 hr, preferably 7-9 hr.

Step 5

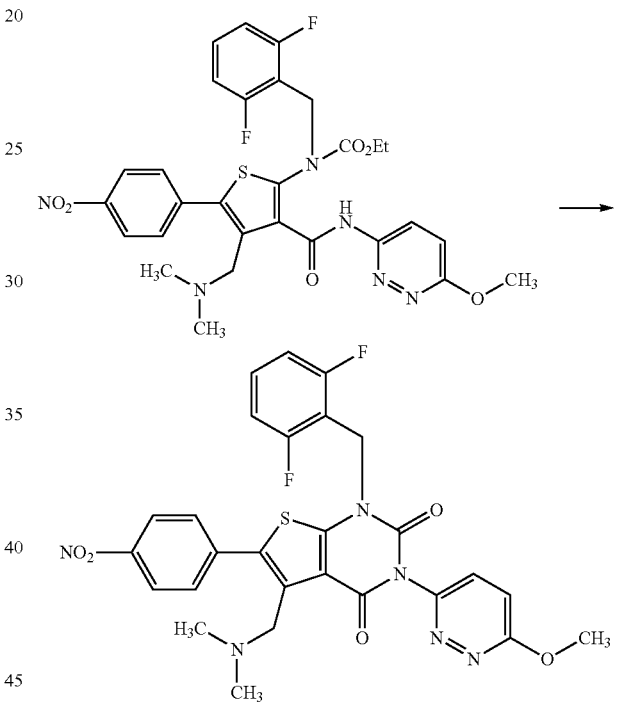

1-(2,6-Difluorobenzyl)-5-dimethylaminomethyl-3-(6-methoxypyridazin-3-yl)-6-(4-nitrophenyl)thieno[2,3-d]pyrimidine-2,4(1H,3H)-dione or a salt thereof (hereinafter to also be referred to as NNTP) can be produced by subjecting NNTC to a cyclization reaction. This reaction is carried out in a solvent. NNTC is compound (I) wherein $R^1$ is a 6-methoxy-3-pyridazinylamino group. NNTP is compound (II) wherein $R^2$ is a nitro group.

The cyclization reaction can be carried out in the presence of a base. The base is not particularly limited, and a base known per se can be used. Examples thereof include sodium methoxide, sodium ethoxide. The amount of the base to be used is generally 0.01-2, preferably 0.02-0.1 equivalents, relative to NNTC.

In another embodiment, the amount of the base to be used is generally 0.05-2, preferably 0.1-1.0 equivalents, relative to NNTC.

The solvent is not particularly limited as long as the reaction proceeds. Examples thereof include methanol, ethanol, tetrahydrofuran, acetonitrile, and mixed solvents thereof. The amount of the solvent to be used is generally 2-30 mL, preferably 3-5 mL, per 1 mmol of NNTC.

In another embodiment, the amount of the solvent to be used is generally 5-30 mL, preferably 10-20 mL, per 1 mmol of NNTC.

The reaction temperature is generally 0-80° C., preferably 20-65° C.

The reaction time is generally 0.5-24 hr, preferably 1-2 hr.

Step 6

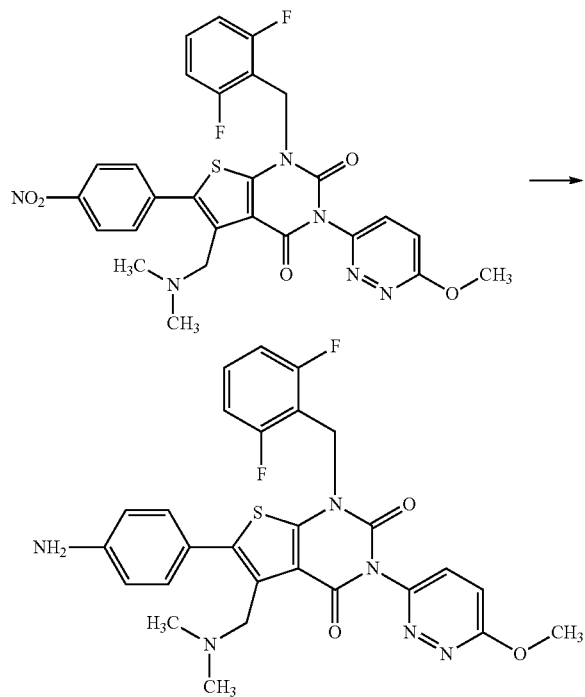

6-(4-Aminophenyl)-1-(2,6-difluorobenzyl)-5-dimethyl-aminomethyl-3-(6-methoxypyridazin-3-yl)thieno[2,3-d]pyrimidine-2,4(1H,3H)-dione or a salt thereof (hereinafter to also be referred to as NATP) can be produced by subjecting NNTP to a reduction reaction. NATP is compound (II) wherein R² is an amino group. NNTP is compound (II) wherein R² is a nitro group.

The reduction reaction can be carried out in the presence of a catalyst. The catalyst is not particularly limited as long as it can be used for a catalytic reduction. Examples thereof include palladium on carbon, palladium hydroxide on carbon, platinum on carbon. The amount of the catalyst to be used is generally 0.01-0.2 g, preferably 0.05-0.2 g, per 1 g of NNTP.

An acid may be added to the reaction system for preferred progress of the reaction. Preferable examples of the acid include hydrochloric acid, hydrogen chloride/methanol solution, formic acid, acetic acid and the like.

In the case of the catalytic reduction, the hydrogen pressure is generally 0.05-0.4 MPa, preferably 0.1-0.3 MPa.

The reduction reaction can also be carried out in a solvent. The solvent is not particularly limited as long as the reaction proceeds. Examples thereof include methanol, ethanol, tetrahydrofuran and the like. The amount of the solvent to be used is generally 1-10 mL, preferably 4-6 mL, per 1 mmol of NNTP.

The reaction temperature is generally 10-40° C., preferably 20-30° C.

The reaction time is generally 1-24 hr, preferably 3-5 hr.

Step 7

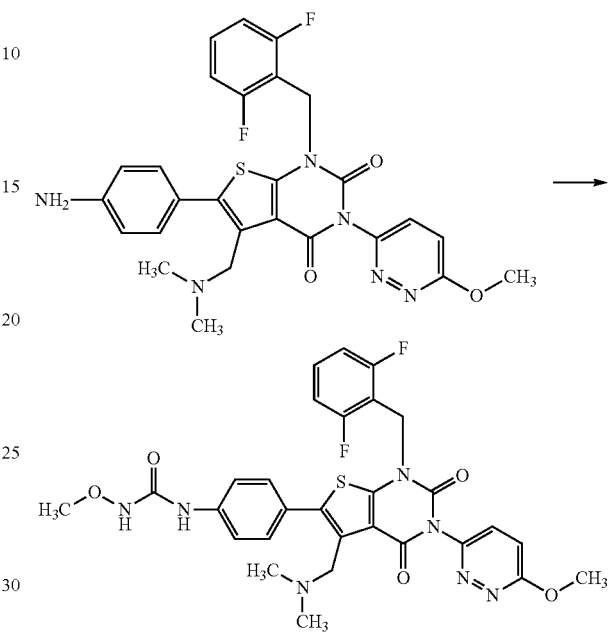

1-{4-[1-(2,6-Difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof can be produced by reacting NATP with 1,1'-carbonyldiimidazole or a salt thereof and methoxyamine or a salt thereof. NATP is compound (II) wherein R² is an amino group.

The amount of the 1,1'-carbonyldiimidazole or a salt thereof to be used is generally 1.0-3.0 equivalents relative to NATP. The lower limit is preferably 1.5 equivalents, more preferably 1.6 equivalents, relative to NATP, and the upper limit is 3.0 equivalents, more preferably 2.5 equivalents, relative to NATP. The preferred range thereof is 1.6-2.5 equivalents, more preferably 1.6-1.8 equivalents, relative to NATP.

The amount of the methoxyamine or a salt thereof (preferably methoxyamine hydrochloride) to be used is generally 1.0-3.0 equivalents relative to 1,1'-carbonyldiimidazole or a salt thereof. The lower limit is preferably 1.05 equivalents, more preferably 1.1 equivalents, relative to 1,1'-carbonyldiimidazole or a salt thereof, and the upper limit is 2.0 equivalents, more preferably 1.5 equivalents, relative to 1,1'-carbonyldiimidazole or a salt thereof. The preferred range thereof is 1.1-1.7 equivalents, more preferably 1.1-1.5 equivalents, relative to 1,1'-carbonyldiimidazole or a salt thereof.

By using 1,1'-carbonyldiimidazole or salt thereof and methoxyamine or a salt thereof in an amount of the abovementioned lower limit or more, the production and residue of the related substance can be suppressed, and therefore, 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof with higher purity can be obtained in higher yield.

In addition, by using 1,1'-carbonyldiimidazole or salt thereof and methoxyamine or a salt thereof in an amount of the above-mentioned upper limit or less, the reaction can be economically carried out.

A base may be used for preferred progress of the reaction. The base is not particularly limited, and a base known per se can be used. Examples thereof include triethylamine, diisopropylethylamine. The amount of the base to be used is generally 0.5-3.0 equivalents, preferably 0.8-0.9 equivalents, relative to NATP.

The reaction can also be carried out in a solvent. The solvent is not particularly limited as long as the reaction proceeds. Examples thereof include acetonitrile, dimethylformamide, dimethylsulfoxide, dichloromethane and the like.

The amount of the solvent to be used is generally 1-10 mL, preferably 2-3 mL, per 1 mmol of NATP.

The reaction temperature is generally 20-60° C., preferably 45-55° C.

The reaction time is generally 1-24 hr, preferably 1-2 hr.

Step 8

Purification of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a Salt Thereof Step 8-1

Production of a Crystal of a Tetrahydrofuran Solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a Salt Thereof A crystal of a tetrahydrofuran solvate of 1-(4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl)-3-methoxyurea or a salt thereof can be produced by recrystallizing 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof from tetrahydrofuran.

Alternatively, the above-mentioned crystal of tetrahydrofuran solvate can also be produced by adding tetrahydrofuran to the reaction mixture after the completion of Step 7.

The amount of the tetrahydrofuran to be used is generally 1-20 mL, preferably 2-10 mL, per 1 g of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof.

The solution or suspension used for the production of the crystal of tetrahydrofuran solvate (hereinafter to also be referred to as crystallization) is stirred generally at 20-80° C., preferably at 40-80° C., more preferably at 30-50° C.

In another embodiment, the solution used for the production of the crystal of tetrahydrofuran solvate (hereinafter to also be referred to as crystallization) is stirred generally at 40-80° C., preferably at 55-65° C.

The solution or suspension used for the crystallization may contain water, and the content of the water is generally greater than 0% and 50% or less, preferably 4-6%, relative to the crude crystals.

The crystallization time is generally 1-24 hr, preferably 1-2 hr.

By drying the obtained crystals according to a method known per se, a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof can be obtained. The drying can be carried out under reduced pressure or in air. The drying temperature is preferably 70° C. or less, more preferably 40-60° C.

Step 8-2

Production of a Crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a Salt Thereof A crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof can be produced by recrystallizing a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof using an alkyl alcohol and one solvent selected from the group consisting of dimethylsulfoxide, dimethylformamide and dimethylacetamide. By washing the obtained crystal with a solvent such as tetrahydrofuran and the like, the crystal with higher purity can also be produced.

The amount of the dimethylsulfoxide, dimethylformamide or dimethylacetamide to be used is generally 1-5 mL, preferably 2-3 mL, per 1 g of the crystal of tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof.

Examples of the alkyl alcohol include a $C_{1-6}$ alkyl alcohol (e.g., ethanol, methanol, isopropyl alcohol) and the like. The alkyl alcohol is preferably ethanol.

The amount of the alkyl alcohol to be used is generally 13-18 mL, preferably 14-16 mL, per 1 g of the crystal of tetrahydrofuran solvate of 1-{4-[1-(2,6-difluorebenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof.

In another embodiment, the amount of the alkyl alcohol to be used is generally 15-20 mL, preferably 16-18 mL, per 1 g of the crystal of tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof.

Examples of the combination of the alkyl alcohol and one solvent selected from the group consisting of dimethylsulfoxide, dimethylformamide and dimethylacetamide include a combination of dimethylsulfoxide and ethanol, a combination of dimethylformamide and ethanol, a combination of dimethylacetamide and ethanol, and the like. The combination is preferably dimethylsulfoxide and ethanol.

The crystallization solution or suspension which is subjected to the recrystallization is stirred generally at 10-50° C., preferably at 15-40° C.

In another embodiment, the crystallization solution is stirred generally at 20-50° C., preferably at 30-40° C.

The crystallization time is generally 1-72 hr, preferably 24-72 hr.

In another embodiment, the crystallization time is generally 1-64 hr, preferably 12-24 hr.

By drying the obtained crystals according to a method known per se, a crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof can be obtained. The drying can be carried out under reduced pressure or in air. The drying temperature is preferably 7° C. or less, more preferably 40-60° C.

By producing a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof from 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof, and then recrystallizing the obtained crystal of tetrahydrofuran solvate using the above-mentioned particular solvents, the contents of the Related Substances 1-3 described in the below-mentioned Examples can be decreased, and therefore, 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof with higher purity can be obtained.

The salt of 1-(4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl-3-methoxyurea is not particularly limited as long as it is acceptable as a medicament. Examples thereof include salts with an inorganic acid (e.g., hydrochloric acid, hydrobromic acid, nitric acid, sulfuric acid, phosphoric acid etc.), and salts with an organic acid (e.g., formic acid, acetic acid, trifluoroacetic acid, fumaric acid, oxalic acid, maleic acid, citric acid, succinic acid, malic acid, methanesulfonic acid, benzenesulfonic acid, p-toluenesulfonic acid etc.).

1-{4-[1-(2,6-Difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof is useful for the prophylaxis or treatment of diseases caused by gonadotropin releasing hormone (e.g., endometriosis, uterine fibroid and prostate cancer), and can be used for the prophylaxis or treatment of the above-mentioned diseases according to the method described in WO 00/56739.

Examples

The present invention is explained in detail in the following by referring to Reference Examples, Examples and Experimental Examples and which are merely exemplified and not to be construed as limitative, and the invention may be changed within the scope of the present invention. In the following Examples, the "room temperature" generally means about 10° C. to about 35° C. The ratios indicated for mixed solvents are volume mixing ratios, unless otherwise specified. % means wt %, unless otherwise specified.

In the following Examples, proton nuclear magnetic resonance spectrum ($^1$H NMR) was measured by Varian Mercury-300 type nuclear magnetic resonance apparatus (300 MHz) using tetramethylsilane as the internal standard. As splitting patterns, singlet, doublet, triplet and multiplet are to abbreviated as s, d, t and m, respectively. The results of the elemental analysis were within ±0.4% of the calculated value. Powder X-ray was measured by D8 ADVANCE (Bruker AXS). High-performance liquid chromatography (HPLC) was measured under condition described in each Reference Example and Example.

Reference Example 1 (Production of 3-amino-6-methoxypyridazine hydrochloride)

Methanol (400 mL), 3-amino-6-chloropyridazine (64.0 g, 0.494 mol) and 28% sodium methoxide methanol solution (114.5 g, 0.593 mol, 1.2 eq) were charged into high pressure reactor, and the mixture was reacted at internal temperature of 130° C. for 8 hr (internal pressure: about 0.7 MPa). The reaction mixture was cooled, conc. hydrochloric acid (12.8 mL) was added dropwise thereto at the temperature not exceeding 40° C., and the mixture was stirred for 20 min. Then, 25% aqueous ammonia (14.9 mL) was added dropwise thereto at the temperature not exceeding 40° C. The reaction mixture was concentrated to about 150 mL under reduced pressure, and isopropyl alcohol (350 mL) was added thereto. Again, the mixture was concentrated to about 150 mL under reduced pressure, isopropyl alcohol (350 mL) was added thereto, and the mixture was stirred for 30 min. The precipitated salt was filtered off, and to the filtrate was added dropwise conc. hydrochloric acid (38.2 mL) at the temperature not exceeding 40° C. The mixture was concentrated to about 200 mL under reduced pressure, and isopropyl alcohol (300 mL) was added thereto. Again, the mixture was concentrated to about 200 mL under reduced pressure, isopropyl alcohol (300 mL) was added thereto, and the mixture was stirred for 30 min. The precipitated crystals were collected by filtration, washed with isopropyl alcohol (50 mL), and dried at 50° C. under reduced pressure until the weight became constant to give a crystal of 3-amino-6-methoxypyridazine hydrochloride (66.9 g, yield: 83.8%, HPLC area percent: 100%).

<HPLC Condition>
detector: ultraviolet absorptiometer (measurement wavelength 254 nm)
column: YMC-Pack ODS-A A-302, 4.6 mm i.d.×150
mobile phase: 0.05M $KH_2PO_4/CH_3CN$=8/2 (v/v)
flow rate: 1.0 mL/min.
measurement time: 30 min
analysis temperature: 25° C.
retention time: 3-amino-6-methoxypyridazine (1.9 min), 3-amino-6-chloropyridazine (2.6 min)

Reference Example 2 (Production of ethyl 2-amino-4-methyl-5-(4-nitrophenyl)thiophene-3-carboxylate)

Toluene (200 mL), 4-nitrophenylacetic acid (100.0 g, 0.552 mol) and N,N'-dimethylformamide (0.42 mL) were heated with stirring, and thionyl chloride (78.8 g, 0.662 mol, 1.2. eq) was added dropwise thereto at internal temperature of 45±5° C. The mixture was stirred at internal temperature of 45±5° C. for 1 hr, and concentrated to about 238 mL under reduced pressure to give an acid chloride solution. Separately, toluene (500 mL), magnesium diethoxide (75.8 g, 0.662 mol, 1.2 eq) and diethyl malonate (106.1 g, 0.662 mol, 1.2 eq) were stirred at internal temperature of 65±5° C. for 0.5 hr, and the mixture was cooled to internal temperature of 40° C. or less. To the solution was added dropwise the total amount of the previously prepared acid chloride solution at internal temperature of 35±5° C., the mixture was stirred at the same temperature for 0.5 hr, and cooled to internal temperature of 30° C. or less, and 2N hydrochloric acid (413 g) was added dropwise thereto at internal temperature of 25±5° C. The mixture was left standing, and the organic layer was separated, washed with 10% brine (400 g), and concentrated to about 250 mL under reduced pressure. To the residue were added acetic acid (176.0 g), water (112 mL) and conc. sulfuric acid (39.0 g), and the mixture was heated with reflux for 4 hr while evaporating volatiles. The mixture was cooled to internal temperature of 15±5° C., ethyl acetate (450 mL) was added thereto, and the pH of the mixture was adjusted to 7.0 with 5N aqueous sodium hydroxide solution at internal temperature of 10-30° C. The mixture was left standing, and the organic layer was separated, washed with 10% brine (100 mL), and concentrated to about 150 mL under reduced pressure. To the residue were added ethanol (240 mL), ethyl cyanoacetate (68.7 g, 0.607 mol, 1.1 eq) and sulfur (19.5 g, 0.607 mol, 1.1 eq), and then n-butylamine (20.2 g, 0.276 mol, 0.5 eq) was added dropwise thereto at internal temperature of 20-45° C. The mixture was stirred at internal temperature of 45±5° C. for 2 hr, cooled to internal temperature of 25±5° C., and stirred at the same temperature for 1 hr. The crystals were collected by filtration, washed with ethanol (200 mL), and dried under reduced pressure at 50° C. or less to give ethyl 2-amino-4-methyl-5-(4-nitrophenyl)thiophene-3-carboxylate (134.9 g, yield: 79.8%, HPLC area percent: 99.2%) as red crystals.

<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4/CH_3CN$=3/7 (v/v)
flow rate: 1.0 mL/min.
measurement time: 45 min
analysis temperature: 25° C.
retention time: ethyl 2-amino-4-methyl-5-(4-nitrophenyl)thiophene-3-carboxylate (5.9 min)

Reference Example 3 (Production of ethyl 2-ethoxycarbonylamino-4-methyl-5-(4-nitrophenyl)thiophene-3-carboxylate)

Ethyl 2-amino-4-methyl-5-(4-nitrophenyl)thiophene-3-carboxylate (130.0 g, 0.424 mol) was suspended in toluene (390 mL), ethyl chloroformate (92.1 g, 0.849 mol, 2.0 eq) was added dropwise thereto while heating with reflux, and the mixture was stirred for 2 hr while heating with reflux. The mixture was cooled to internal temperature of 55±5° C., ethanol (1170 mL) was added dropwise thereto at the same temperature, and the mixture was cooled to internal temperature of 5±15° C., and stirred at the same temperature for 1 hr. The crystals were collected by filtration, washed with ethanol (260 mL), and dried at 45° C. under reduced pressure to give ethyl 2-ethoxycarbonylamino-4-methyl-5-(4-nitrophenyl)thiophene-3-carboxylate (154.2 g, yield: 96.1%, HPLC area percent: 99.9%) as yellow crystals.

<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4/CH_3CN$=3/7 (v/v)
flow rate: 1.0 mL/min.
measurement time: 45 min
analysis temperature: 25° C.
retention time: ethyl 2-amino-4-methyl-5-(4-nitrophenyl)thiophene-3-carboxylate (5.9 min), ethyl 2-ethoxycarbonylamino-4-methyl-5-(4-nitrophenyl)thiophene-3-carboxylate (16.5 min)

Reference Example 4 (Production of ethyl 2-[(2,6-difluorobenzyl)ethoxycarbonylamino]-4-methyl-5-(4-nitrophenyl)thiophene-3-carboxylate)

Ethyl 2-ethoxycarbonylamino-4-methyl-5-(4-nitrophenyl)thiophene-3-carboxylate (150.0 g, 0.396 mol) was suspended in N,N'-dimethylacetamide (450 mL), and potassium carbonate (60.3 g, 0.436 mol, 1.1 eq) and 35% 2,6-difluorobenzyl bromide/acetonitrile solution (257.9 g, 0.436 mol, 1.1 eq) were added thereto. The mixture was heated with stirring at internal temperature of 85±5° C. for 2 hr, and cooled to internal temperature of 55±5° C., and ethyl acetate (1200 mL) and water (750 mL) were added thereto. The mixture was left standing, and the organic layer was separated, washed with water (750 mL), and concentrated to about 420 mL under reduced pressure. To the residue was added heptane (945 mL), and the mixture was stirred at internal temperature of 45±5° C. for 1 hr, and then at internal temperature of 5±5° C. for 1 hr. The crystals were collected by filtration, washed with ethyl acetate/heptane (1/3, 300 mL) of 5±5° C., and dried at 45±5° C. under reduced pressure to give ethyl 2-[(2,6-difluorobenzyl)ethoxycarbonylamino]-4-methyl-5-(4-nitrophenyl)thiophene-3-carboxylate (190.7 g, yield: 95.5%, HPLC area percent: 99.9%) as pale yellow crystals.

<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4/CH_3CN$=3/7 (v/v)
flow rate: 1.0 mL/min.
measurement time: 30 min
analysis temperature: 25° C.
retention time: ethyl 2-[(2,6-difluorobenzyl)ethoxycarbonylamino]-4-methyl-5-(4-nitrophenyl)thiophene-3-carboxylate (10.7 min), ethyl 2-ethoxycarbonylamino-4-methyl-5-(4-nitrophenyl)thiophene-3-carboxylate (16.4 min)

Example 1 (Production of ethyl 4-bromomethyl-2-[(2,6-difluorobenzyl)ethoxycarbonylamino]-5-(4-nitrophenyl)thiophene-3-carboxylate)

Ethyl 2-[(2,6-difluorobenzyl)ethoxycarbonylamino]-4-methyl-5-(4-nitrophenyl)thiophene-3-carboxylate (1100.0 g, 2.180 mol) was suspended in a mixed solvent of ethyl acetate (8.8 L) and trifluoromethylbenzene (880 mL), N-bromosuccinimide (NBS, 485.1 g, 2.725 mol, 1.25 eq) and 2,2'-azobis(2,4-dimethylvaleronitrile) (V-65, 54.2 g, 0.218 mol, 0.1 eq) were added thereto. The reaction mixture was heated with stirring at 65-75° C. for 40 min. The reaction mixture was cooled to 25±5° C., and washed twice with city water (4.3 L). The ethyl acetate layer was concentrated to about 4 L under reduced pressure. Ethanol (3 L) was added thereto, and the mixture was concentrated to about 4 L under reduced pressure. Again, ethanol (3 L) was added thereto, and the mixture was concentrated to about 4 L under reduced pressure. Heptane (1.76 L) was added thereto, and the mixture was stirred at 25±5° C. for 30 min. Again, heptane (1.32 L) was added thereto, and the mixture was stirred at 5±5° C. for 1 hr. The crystals were collected by filtration, washed with ethanol/heptane (1/2, 1.76 L), and dried at 45±5° C. under reduced pressure to give ethyl 4-bromomethyl-2-[(2,6-difluorobenzyl)ethoxycarbonylamino]-5-(4-nitrophenyl)thiophene-3-carboxylate (1171 g, yield: 92.1%, HPLC area percent: 92.9%) as pale yellow crystals.

<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4/CH_3CN$=3/7 (v/v) flow rate: 1.0 mL/min.
measurement time: 30 min
analysis temperature: 25° C.

retention time: ethyl 2-[(2,6-difluorobenzyl)ethoxycarbonylamino]-4-methyl-5-(4-nitrophenyl)thiophene-3-carboxylate (11.0 min), ethyl 4-bromomethyl-2-[(2,6-difluorobenzyl) ethoxycarbonylamino]-5-(4-nitrophenyl)thiophene-3-carboxylate (12.3 min)

Example 2 (Production of ethyl 2-[(2,6-difluorobenzyl) ethoxycarbonylamino]-4-dimethylaminomethyl-5-(4-nitrophenyl)thiophene-3-carboxylate)

Dimethylamine hydrochloride (2.10 g, 25.71 mmol, 1.5 eq) was suspended in N,N'-dimethylformamide (DMF, 55 mL), triethylamine (4.51 g, 44.57 mmol, 2.6 eq) was added thereto, and the mixture was stirred at 25±5° C. for 30 min. The mixture was cooled to 5±5° C., and ethyl 4-bromomethyl-2-[(2,6-difluorobenzyl)ethoxycarbonylamino]-5-(4-nitrophenyl)thiophene-3-carboxylate (10 g, 17.14 mmol) was added thereto, and the container used for the compound was washed with DMF (5 mL). The reaction mixture was stirred at 15±5° C. for 1 hr. Ethanol (20 mL) was added thereto at 20±10° C., and the mixture was warmed to internal temperature of 40±5° C. City water (25 mL) was added thereto at internal temperature of 40±5° C., and the mixture was stirred at the same temperature for 1 hr, and then at 25-5° C. for 1 hr. The crystals were collected by filtration, washed with ethanol/city water (4/1, 15 mL), and dried at 50±5° C. under reduced pressure to give ethyl 2-[(2,6-difluorobenzyl)ethoxycarbonylamino]-4-dimethylaminomethyl-5-(4-nitrophenyl)thiophene-3-carboxylate (8.41 g, yield: 89.6%, HPLC area percent: 99.6%) as yellow crystals.
<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4$/$CH_3CN$=3/7 (v/v)
flow rate: 1.0 mL/min.
measurement time: 30 min
analysis temperature: 25° C.
retention time: ethyl 2-[(2,6-difluorobenzyl)ethoxycarbonylamino]-4-dimethylaminomethyl-5-(4-nitrophenyl)thiophene-3-carboxylate (2.3 min), ethyl 4-bromomethyl-2-[(2,6-difluorobenzyl)ethoxycarbonylamino]-5-(4-nitrophenyl)thiophene-3-carboxylate (13.1 min)
$^1$H-NMR (CDCl$_3$) δ: 1.10-1.30 (3H, m), 1.31 (3H, t, J=7.2 Hz), 2.07 (6H, s), 3.51 (2H, s), 4.10-4.30 (2H, m), 4.23 (2H, q, J=7.2 Hz), 5.02 (2H, s), 6.85 (2H, t, J=8.0 Hz), 7.66 (2H, d, J=9.0 Hz), 8.24 (2H, d, J=9.0 Hz).

Example 3 (Production of 2-[(2,6-difluorobenzyl) ethoxycarbonylamino]-4-dimethylaminomethyl-5-(4-nitrophenyl)thiophene-3-carboxylic acid)

Ethyl 2-[(2,6-difluorobenzyl)ethoxycarbonylamino]-4-dimethylaminomethyl-5-(4-nitrophenyl)thiophenyl)thiophene-3-carboxylate (8.0 g, 14.61 mmol) was suspended in a mixed solvent of ethanol (72 mL) and city water (20.8 mL), 48% aqueous potassium hydroxide solution (2.56 g, 21.92 mmol, 1.5 eq) was added thereto, and the mixture was stirred at 60±5° C. for 5 hr. The reaction mixture was cooled to 25±5° C., and the pH of the mixture was adjusted to 6.0-7.0 with 6N hydrochloric acid. The mixture was concentrated to about 28 mL at 50° C. or less under reduced pressure, and ethanol (4 mL) and ethyl acetate (4 mL) were added thereto at internal temperature of 40±5° C. Then, city water (48 mL) was added thereto at the same temperature, and the mixture was stirred at the same temperature for 1 hr. The mixture was cooled to internal temperature of 25±5° C., and stirred at the same temperature for 3 hr. The crystals were collected by filtration, washed successively with ethanol/city water (1/9, 24 mL) and cooled ethyl acetate (24 mL), and dried at 45±5° C. under reduced pressure to give 2-[(2,6-difluorobenzyl)ethoxycarbonylamino]-4-dimethylaminomethyl-5-(4-nitrophenyl)thiophene-3-carboxylic acid (6.82 g, yield: 89.9%, HPLC area percent: 98.7%) as yellow crystals.
<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4$/$CH_3CN$=6/4 (v/v)
flow rate: 1.0 mL/min.
measurement time: 30 min
analysis temperature: 25° C.
retention time: 2-[(2,6-difluorobenzyl)ethoxycarbonylamino]-4-dimethylaminomethyl-5-(4-nitrophenyl)thiophene-3-carboxylic acid (8.4 min), ethyl 2-[(2,6-difluorobenzyl)ethoxycarbonylamino]-4-dimethylaminomethyl-5-(4-nitrophenyl)thiophene-3-carboxylate (14.8 min)
$^1$H-NMR (CDCl$_3$) δ: 1.10-1.40 (3H, m), 2.37 (6H, s), 3.72 (2H, s), 4.10-4.35 (2H, m), 5.07 (2H, s), 6.84 (2H, t, J=7.5 Hz), 7.15-7.30 (1H, m), 7.42 (2H, d, J=8.8 Hz), 8.29 (2H, d, J=8.8 Hz).

Example 4 (Production of ethyl (2,6-difluorobenzyl)-[4-dimethylaminomethyl-3-(6-methoxypyridazin-3-ylcarbamoyl)-5-(4-nitrophenyl)thiophen-2-yl]carbamate)

Under a nitrogen atmosphere, 2-[(2,6-difluorobenzyl)ethoxycarbonylamino]-4-dimethylaminomethyl-5-(4-nitrophenyl)thiophene-3-carboxylic acid (6.5 g, 12.51 mmol) and 3-amino-6-methoxypyridazine hydrochloride (2.43 g, 15.01 mmol, 1.2 eq) were added to N,N'-dimethylacetamide (DMAc, 29.25 mL), and then ethyldiisopropylamine (4.03 g, 31.28 mmol, 2.5 eq) was added thereto at 25±15° C. The mixture was warmed to internal temperature of 55±5° C., and stirred for 30 min. 50.5% Propylphosphonic anhydride (T3P) ethyl acetate solution (9.55 g, 15.01 mmol, 1.2 eq) was added dropwise thereto at internal temperature of 60° C. or less, and the container used for the reagent was washed with DMAc (3.25 mL). The mixture was stirred at internal temperature of 55±5° C. for 1 hr. The reaction mixture was cooled to 25±5° C., and city water (48.75 mL) was added dropwise thereto at the same temperature. Then, 8N aqueous sodium hydroxide solution was added thereto at 25±5° C. while vigorously stirring, and the pH of the mixture was adjusted to 7.5-8.5, and the mixture was stirred at 25±5° C. for 30 min. The crystals were collected by filtration, washed with methanol (26 mL), and dried at 40±5° C. under reduced pressure until the weight became constant to give ethyl (2,6-difluorobenzyl)-[4-dimethylaminomethyl-3-(6-methoxypyridazin-3-ylcarbamoyl)-5-(4-nitrophenyl)thiophen-2-yl]carbamate (7.61 g, yield: 97.0%, HPLC area percent: 98.5%) as yellow crystals.
<HPLC Condition>
detector: ultraviolet absorptiometer (measurement wavelength 254 nm)
column: YMC ODS-A A-302, 4.6 mm i.d.×150 mm
mobile phase: 0.02M $KH_2PO_4$/$CH_3CN$=4/6 (v/v)
flow rate: 1.0 mL/min.
measurement time: 40 min
analysis temperature: 25° C.
retention time: 3-amino-6-methoxypyridazine (1.7 min), 2-[(2,6-difluorobenzyl)ethoxycarbonylamino]-4-dimethylaminomethyl-5-(4-nitrophenyl)thiophene-3-carboxylic acid (2.5 min), ethyl (2,6-difluorobenzyl)-[4-dimethylaminomethyl-3-(6-methoxypyridazin-3-ylcarbamoyl)-5-(4-nitrophenyl)thiophen-2-yl]carbamate (15.0 min)

$^1$H-NMR (CDCl$_3$) δ: 1.10-1.40 (3H, m), 2.20 (6H, s), 3.51 (2H, s), 4.10 (3H, m), 4.20-4.35 (2H, m), 5.03 (2H, s), 6.70-6.80 (2H, m), 6.99 (1H, d, J=9.5 Hz), 7.10-7.20 (1H, m), 7.45-7.55 (2H, m), 8.25-8.35 (2H, m), 8.54 (1H, d, J=9.5 Hz).

Example 5 (Production of 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione hydrochloride)

Ethyl (2,6-difluorobenzyl)-[4-dimethylaminomethyl-3-(6-methoxypyridazin-3-ylcarbamoyl)-5-(4-nitrophenyl) thiophen-2-yl]carbamate (7.5 g, 11.97 mmol), methanol (187.5 mL, 25 v/w), tetrahydrofuran (12.75 mL, 1.7 v/w) and 28% sodium methoxide methanol solution (0.46 g, 2.39 mmol, 0.2 eq) were stirred at 60±5° C. for 1 hr. The mixture was cooled to 25±5° C., conc. hydrochloric acid (2.87 g, 28.73 mmol, 2.4 eq) was added dropwise thereto, and the mixture was stirred for 20 min. Isopropyl alcohol (75 mL) was added thereto, and the mixture was stirred at 25±5° C. for 20 min, and then at 5±5° C. for 40 min. The crystals were collected by filtration, washed with cooled methanol/isopropyl alcohol (1/1, 22.5 mL), and dried at internal temperature of 60° C. or less (external temperature 55±5° C.) under reduced pressure to give 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione hydrochloride (7.24 g, yield: 98.0%, HPLC area percent: 99.9%) as yellow crystals.
<HPLC Condition>
detector: ultraviolet absorptiometer (measurement wavelength 254 nm)
column: YMC ODS-A A-302, 4.6 mm i.d.×150 mm
mobile phase: 0.02M KH$_2$PO$_4$/CH$_3$CN=4/6 (v/v)
flow rate: 1.0 mL/min.
measurement time: 40 min
analysis temperature: 25° C.
retention time: ethyl (2,6-difluorobenzyl)-[4-dimethylaminomethyl-3-(6-methoxypyridazin-3-ylcarbamoyl)-5-(4-nitrophenyl)thiophen-2-yl]carbamate (15.0 min), 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione (2.5 min)

$^1$H-NMR (CDCl$_3$) δ: 2.20 (6H, s), 3.72 (2H, s), 4.19 (3H, s), 5.38 (2H, brs), 6.95 (2H, t, J=8.2 Hz), 7.14 (1H, d, J=9.0 Hz), 7.20-7.35 (1H, m), 7.42 (i, d, J=9.0 Hz), 7.89 (2H, d, J=8.8 Hz), 8.28 (2H, d, J=8.8 Hz).

Example 6 (Production of 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (in the present specification, to also be referred to as RS-2 (Related Substance 2)))

To 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione hydrochloride (80.0 g, 129.66 mmol) were added methanol (640 mL) and conc. hydrochloric acid (10.8 g, 103.68 mmol, 0.8 eq). 10% Pd—C NX type (8.0 g, containing 50% water) was added thereto under nitrogen atmosphere, and the mixture was stirred at 25-5° C. for 4 hr under hydrogen pressure of 0.2±0.1 MPa. The pH of the mixture was adjusted to 6.5±0.5 with triethylamine at 25±5° C. Activated carbon (Shirasagi A, 4.0 g) was added thereto, and the mixture was stirred for 20-60 min. The activated carbon and catalyst were filtered off, and washed with methanol (160 mL). The filtrate was warmed to 40±5° C., and the pH of the mixture was adjusted to 8.0-8.5 with triethylamine. The mixture was aged with stirring at 40±5° C. for about 30 min, cooled to 5±5° C., and aged with stirring for about 2 hr. The crystals were collected by filtration, washed with methanol (160 mL), and dried at 45±5° C. under reduced pressure until the weight became constant to give an almost white crystal of 6-(4-aminophenyl)-1-(2,6-difluorobenzyl-5-dimethyl-5-dimethylaminomethyl-3-(6-methoxypyridazin-3-yl) thieno[2,3-d]pyrimidine-2,4(1H,3H)-dione (60.06 g, yield: 84.1%, HPLC area percent: 99%).
<HPLC Condition>
detector: ultraviolet absorptiometer (measurement wavelength 254 nm)
column: YMC ODS-A A-302, 4.6 mm i.d.×150 mm
mobile phase: 0.05M KH$_2$PO$_4$ (pH7.0 by 10% KOH)/CH$_3$CN=55/45 (v/v)
flow rate: 1.0 mL/min.
measurement time: 30 min
analysis temperature: 25° C.
retention time: 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (4.0 min), 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione (16 min)

$^1$H-NMR (CDCl$_3$) δ: 2.09 (6H, s), 3.40-3.70 (2H, br), 3.78 (2H, s), 4.14 (3H, s), 5.31 (2H, brs), 6.66 (2H, d, J=8.6 Hz), 6.88 (2H, t, J=7.6 Hz), 7.07 (1H, d, J=9.2 Hz), 7.15-7.25 (1H, m), 7.27 (2H, d, J=8.0 Hz), 7.38 (1H, d, J=9.2 Hz).

Example 7 (Production of a Crystal of a Tetrahydrofuran Solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea)

Acetonitrile (30 mL) and 1,1'-carbonyldiimidazole (CDI, 5.01 g, 30.90 mmol, 1.7 eq) were charged into a reactor, and the mixture was stirred. Triethylamine (1.56 g, 15.42 mmol, 0.85 eq) was added thereto with stirring, and cooled to internal temperature of 10±5° C. Methoxyamine hydrochloride (2.90 g, 34.72 mmol, 1.91 eq) was added thereto with stirring in some portions at internal temperature of 30° C. or less, and the container used for the reagent was washed with acetonitrile (5 mL). The mixture was stirred at internal temperature of 25±5° C., and after confirming the dissolution of the mixture, the solution was stirred for additional 10 min or more. Then, 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (10.00 g, 18.16 mmol) was added thereto with stirring, and the container used for the reagent was washed with acetonitrile (5 mL). The reaction mixture was warmed to internal temperature of 50±5° C., and stirred at the same temperature for 2 hr to give a reaction mixture (hereinafter to be referred to as Reaction Mixture A). Triethylamine (2.35 g, 23.22 mmol, 1.28 eq) was added thereto with stirring at internal temperature of 50±5° C. City water (40 mL) was added dropwise thereto at internal temperature of 40-55° C., the mixture was stirred for 1 hr, and city water (100 mL) was added dropwise again thereto at internal temperature of 40-55° C. The mixture was aged with stirring at internal temperature of 25±5° C. for 1 hr or more. The crystals were collected by filtration, and washed with a mixed solvent of city water (16 mL) and acetonitrile (4 mL) to give wet crystals. To the wet crystals was added tetrahydrofuran (50 mL), and the mixture was warmed to internal temperature of 60±5° C., and stirred at the same temperature for about 1 hr. The mixture was cooled to internal temperature of 5±5° C., and aged with stirring at the same temperature for about 2 hr. The crystals were collected by filtration, washed with tetrahydrofuran (10 mL), and dried at external temperature 50±10° C. under reduced pressure to give a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (11.49 g, yield 90.9%).

$^1$H-NMR (CDCl$_3$) δ: 1.80-1.90 (4H, m), 2.13 (6H, s), 3.60-3.80 (6H, m), 3.82 (3H, s), 4.18 (3H, s), 5.35 (2H, brs), 6.92 (2H, t, J=8.2 Hz), 7.12 (1H, d, J=8.8 Hz), 7.20-7.60 (7H, m), 7.65 (1H, s).

Anal Calcd for C$_{33}$H$_{35}$F$_2$N$_7$O$_6$S: C, 56.97; H, 5.07; N, 14.09. Found: C, 56.81; H, 5.17; N, 13.92.

The powder X-ray diffraction pattern of the above-mentioned crystal of tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea is shown in FIG. 1.

<Measurement Condition for Powder X-Ray Diffraction>
tube voltage: 40 kV
tube current: 40 mA
gate time: 0.2 sec/step
step width: 0.02°
scanning field: 2θ=3-40°

In addition, the characteristic peaks of the powder X-ray diffraction pattern are shown in Table 1.

TABLE 1

| 2θ (°) | d value (Å) | relative intensity (%) |
|---|---|---|
| 7.285 | 12.125 | 85.9 |
| 8.302 | 10.642 | 40.2 |
| 10.597 | 8.342 | 72.4 |
| 13.605 | 6.504 | 41.1 |
| 15.292 | 5.790 | 100.0 |
| 18.792 | 4.718 | 44.9 |
| 23.059 | 3.854 | 31.7 |
| 25.144 | 3.539 | 20.4 |
| 29.294 | 3.047 | 18.1 |

Example 8 (Production of a crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea)

Dimethylsulfoxide (DMSO, 20 mL) and a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (8.93 g) were charged into a reactor, and the mixture was dissolved by warming to internal temperature of 35±5° C. After confirming the dissolution of the mixture, ethanol (20 mL) was added thereto at internal temperature of 35±5° C. The mixture was filtered through a dust removal filter, and washed with ethanol (8 mL). To the filtrate was added ethanol (112 mL) at internal temperature of 35±50° C., and the mixture was stirred at internal temperature of 35±5° C. for 1 hr or more, cooled to internal temperature of 25±5° C., and stirred again at the same temperature for 12 hr or more. The crystals were collected by filtration, washed with ethanol (16 mL), and dried at external temperature 50±10° C. under reduced pressure to give 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (7.33 g, yield 91.6%) as white crystals.

Figure 2:
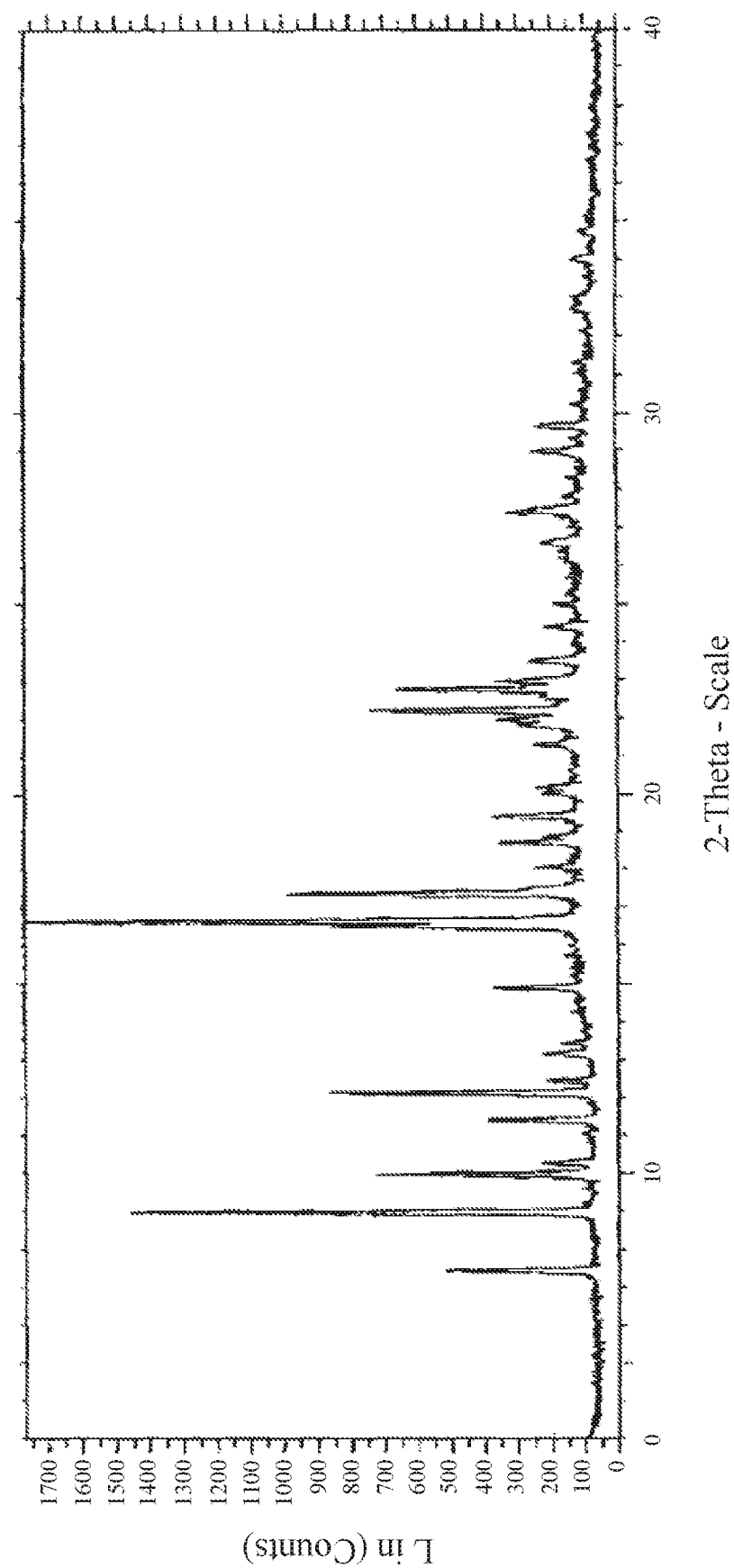
FIG. 2 shows a powder X-ray diffraction pattern of a crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea.

The powder X-ray diffraction pattern of the above-mentioned white crystal is shown in FIG. 2.

<Measurement Condition for Powder X-Ray Diffraction>
tube voltage: 40 kV
tube current: 40 mA
gate time: 0.2 sec/step
step width: 0.02°
scanning field: 2θ=3-40°

In addition, the characteristic peaks of the powder X-ray diffraction pattern are shown in Table 2.

TABLE 2

| 2θ (°) | d value (Å) | relative intensity (%) |
|---|---|---|
| 7.384 | 11.963 | 29.1 |
| 8.932 | 9.893 | 82.6 |
| 9.933 | 8.898 | 40.9 |
| 12.076 | 7.323 | 48.8 |
| 16.607 | 5.334 | 100.0 |
| 17.328 | 5.114 | 55.8 |
| 22.202 | 4.001 | 41.5 |
| 22.761 | 3.904 | 37.2 |
| 27.422 | 3.245 | 18.4 |

Example 9

The experiment was carried out in the same manner as in Example 7, except that the equivalents (eq) of 1,1'-carbonyldiimidazole (CDI) and methoxyamine hydrochloride were changed. The contents of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (in the table, to be referred to as "Compound A") and RS-2 in Reaction Mixture A obtained in the above-mentioned experiment are shown in Table 4. The equivalent of CDI in the table means one relative to NATP, and the equivalent of methoxyamine hydrochloride means one relative to CDI.

HPLC measurement condition in Example 9 and Experimental Example 1 is shown in the following.

<HPLC Condition>
detector: ultraviolet absorptiometer (measurement wavelength 230 nm)
column: Sunfire C18 S-3.5 μm, 4.6 mm i.d.×10 cm (manufactured by Waters)
mobile phase: (A) a mixed solvent of 0.05 mol/L phosphorate buffer solution (pH2.0)/acetonitrile (31:9 (volume ratio))
(B) a mixed solvent of 0.05 mol/L phosphorate buffer solution (pH2.0)/acetonitrile (12:13 (volume ratio))
Gradient Program (Linear)

TABLE 3

| Time (min) | A solution (%) | B solution (%) |
|---|---|---|
| 0 (injection) | 100 | 0 |
| 20 | 100 | 0 |

TABLE 3-continued

| Time (min) | A solution (%) | B solution (%) |
|---|---|---|
| 55 | 0 | 100 |
| 55.1 | 100 | 0 |
| 65 | 100 | 0 | flow rate: 1.0 mL/min.
measurement time: 60 min
analysis temperature: 40° C.
retention time: 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (7.3 min), 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (15.5 min)

TABLE 4

| NATP | CDI | methoxyamine hydrochloride | Compound A HPLC area percent (%) | RS-2 |
|---|---|---|---|---|
| 1 eq | 1.5 eq | 1.127 eq | 93.38% | 4.45% |
| 1 eq | 1.6 eq | 1.125 eq | 96.70% | 0.25% |
| 1 eq | 1.7 eq | 1.125 eq | 95.15% | 0.20% |
| 1 eq | 1.8 eq | 1.125 eq | 93.89% | 0.22% |
| 1 eq | 2.0 eq | 1.125 eq | 92.56% | 0.23% |
| 1 eq | 2.5 eq | 1.124 eq | 90.28% | 0.20% |

As can be seen in Table 4, it was found that, in the production shown in Example 7, 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea with high quality, which has low content of RS-2, can be obtained by using CDI of 1.6 to 2.5 equivalents relative to NATP and methoxyamine hydrochloride of 1.1 to 1.5 equivalents relative to CDI.

Experimental Example 1

The contents of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (in the table, to be referred to as "Compound A") and the related substances (specifically RS-1, RS-2 and RS-3) in each crystal obtained Examples 7 and 8 were measured. The results are shown in Table 5.

TABLE 5

| | HPLC area percent (%) | | | |
|---|---|---|---|---|
| Sample | RS-1 | RS-2 | Compound A | RS-3 |
| a wet crystal of Example 7 | 0.10 | 0.16 | 99.37 | 0.08 |
| a crystal of a tetrahydrofuran solvate of Example 7 | 0.04 | 0.07 | 99.75 | 0.02 |
| a white crystal of Example 8 | 0.02 | 0.05 | 99.81 | <0.02 |

As can be seen in Table 5, the contents of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea in the crystal of tetrahydrofuran solvate obtained in Example 7 and the white crystal obtained in Example 8 are high as compared with the wet crystal obtained in Example 7. From this evidence, it was found that 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea with high quality, which has low contents of the related substances, can be obtained by the methods described in Example 7 and Example 8.

Example 10 (Production of 1-{4-[1-(2,6-difluorobenzyl)-5-dimethylaminomethyl-2,4-dioxo-3-(6-oxo-1,6-dihydropyridazin-3-yl)-1,2,3,4-tetrahydrothieno[2,3-d]pyrimidin-6-yl]phenyl}-3-methoxyurea (in the Present Specification, to Also be Referred to as RS-1 (Related Substance 1)))

1-{4-[1-(2,6-Difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (0.50 g, 0.80 mmol) was dissolved in DMSO (1.5 mL), and conc. hydrochloric acid (0.32 g, 3.2 mmol) was added thereto. The reaction mixture was stirred at 80° C. for 2 hr. Aqueous sodium bicarbonate solution (0.27 g, 3.2 mmol) and water (3 mL) were added thereto at room temperature, and the precipitate was collected by filtration, and washed with water (30 mL), and dried at 50° C. under reduced pressure to give a crystal of 1-{4-[1-(2,6-difluorobenzyl)-5-dimethylaminomethyl-2,4-dioxo-3-(6-oxo-1,6-dihydropyridazin-3-yl)-1,2,3,4-tetrahydrothieno[2,3-d]pyrimidin-6-yl]phenyl}-3-methoxyurea (0.19 g, 39%).
$^1$H-NMR (CDCl$_3$) δ: 2.06 (6H, s), ca. 3.54 (1H, m), ca. 3.63 (1H, m), 3.65 (3H, s), ca. 5.18 (1H, m), ca. 5.40 (1H, m), 7.07 (1H, d, J=9.8 Hz), ca. 7.14 (1H, m), ca. 7.47 (1H, m), ca. 7.51 (1H, m), ca. 7.52 (2H, m), ca. 7.72 (2H, m), 9.08 (1H, s), 9.63 (1H, s), 13.29 (1H, s).
IR (KBr): 1719, 1676, 1591, 1528, 1470, 1410, 1331, 1034 cm$^{-1}$.
ESI-MS m/z: 610.17 [M+H]$^+$, 608.15 [M−H]$^−$.
Anal Calcd for $C_{27}H_{24}F_2N_6O_3S \cdot 0.1H_2O$: C, 58.71; H, 4.42; N, 15.21. Found: C, 58.43; H, 4.39; N, 15.19.

Example 11 (Production of N-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-N,N'-dimethoxydicarbonimidic diamide (in the Present Specification, to Also be Referred to as RS-3 (Related Substance 3)))

RS-3 was separated from crude 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea by HPLC, and the structure was determined by the following spectrum data.
$^1$H-NMR (CDCl$_3$) δ: 2.05 (6H, s), ca. 3.54 (1H, m), ca. 3.67 (1H, m), 3.70 (3H, s), 3.80 (3H, s), 4.10 (3H, s), ca. 5.22 (1H, m), ca. 5.39 (1H, m), ca. 7.14 (2H, m), ca. 7.46 (1H, m), ca. 7.47 (1H, m), ca. 7.62 (2H, m), ca. 7.64 (2H, m), ca. 7.76 (1H, m), 10.30 (1H, s), 11.34 (1H, s).
IR (KBr): 1714, 1674, 1591, 1528, 1460, 1410, 1306, 1036 cm$^{-1}$.
ESI-MS m/z: 697.20 [M+H]$^+$, 719.18 [M+Na]$^+$.
Anal Calcd for $C_{31}H_{30}F_2N_8O_7S \cdot 1.0H_2O$: C, 52.10; H, 4.51; N, 15.68. Found: C, 52.17; H, 4.52; N, 15.78.

Example 12 (Production of ethyl 4-bromomethyl-2-[(2,6-difluorobenzyl)ethoxycarbonylamino]-5-(4-nitrophenyl)thiophene-3-carboxylate)

Ethyl 2-[(2,6-difluorobenzyl)ethoxycarbonylamino]-4-methyl-5-(4-nitrophenyl)thiophene-3-carboxylate (50 g, 99.11 mmol) was suspended in a mixed solvent of ethyl acetate (300 mL) and trifluoromethylbenzene (40 mL), and the mixture was purged with nitrogen. A suspension of N-bromosuccinimide (NBS, 22.05 g, 123.89 mmol, 1.25 eq) and 2,2'-azobis(2,4-dimethylvaleronitrile) (V-65, 1.97 g, 7.93 mmol, 0.08 eq) in ethyl acetate (90 mL) was added thereto at internal temperature of 70±5° C., and the container used for the suspension was washed with ethyl acetate (10 mL).

The reaction mixture was heated with stirring at 65-75° C. for 40 min. The reaction mixture was cooled to 25±5° C., and washed twice with city water (195 mL). The ethyl acetate layer was concentrated to about 165 mL under reduced pressure. Ethanol (135 mL) was added thereto, and the mixture was concentrated to about 155 mL under reduced pressure. Ethanol (135 mL) was added again thereto, and then heptane (130 mL) was added thereto, and the mixture was stirred at 25±5° C. for 30 min. Heptane (100 mL) was added again thereto, and the mixture was stirred at 5±5° C. for 1 hr. The crystals were collected by so filtration, washed with ethanol/heptane (1/2, 80 mL), and dried at 45±5° C. under reduced pressure to give ethyl 4-bromomethyl-2-[(2,6-difluorobenzyl)ethoxycarbonylamino]-5-(4-nitrophenyl)thiophene-3-carboxylate (50.4 g, yield: 92.1%, HPLC area percent: 94.3%) as pale yellow crystals.
<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4/CH_3CN$=3/7 (v/v)
flow rate: 1.0 mL/min.
measurement time: 40 min
analysis temperature: 25° C.
retention time: ethyl 2-[(2,6-difluorobenzyl)ethoxycarbonylamino]-4-methyl-5-(4-nitrophenyl)thiophene-3-carboxylate (11.5 min), ethyl 4-bromomethyl-2-[(2,6-difluorobenzyl)ethoxycarbonylamino]-5-(4-nitrophenyl)thiophene-3-carboxylate (13 min)

Example 13 (Production of 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione hydrochloride)

Ethyl (2,6-difluorobenzyl)-[4-dimethylaminomethyl-3-(6-methoxypyridazin-3-ylcarbamoyl)-5-(4-nitrophenyl)thiophen-2-yl]carbamate (30.0 g, 47.88 mmol) was suspended in acetonitrile (210 mL), 28% sodium methoxide methanol solution (0.46 g, 2.39 mmol, 0.05 eq) was added thereto at internal temperature of 25±5° C., and the container used for the reagent was washed with methanol (0.3 mL). The mixture was stirred at internal temperature of 25±5° C. for 1 hr, and the crystals were collected by filtration, and washed with acetonitrile (60 mL) to give 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione.

Methanol (90 mL), isopropyl alcohol (150 mL) and conc. hydrochloric acid (5.49 g, 52.66 mmol, 1.1 eq) were charged into a reactor, the total amount of 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione was added thereto at internal temperature of 25±5° C., and the container used for the compound was washed with isopropyl alcohol (30 mL). The mixture was stirred at internal temperature of 25±5° C. for 0.5 hr, cooled to internal temperature of 5±5° C., and stirred at the same temperature for 1 hr. The crystals were collected by filtration, washed with methanol/isopropyl alcohol (1/2, 60 mL, cooled to 5±5° C.), and dried at 50±5° C. under reduced pressure to give 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione hydrochloride (29.3 g, yield: 99.2%, HPLC area percent: 99.8%) as yellow crystals.
<HPLC Condition>
detector: ultraviolet absorptiometer (measurement wavelength 254 nm)
column: YMC ODS-A A-302, 4.6 mm i.d.×150 mm
mobile phase: 0.02M $KH_2PO_4/CH_3CN$=4/6 (v/v)
flow rate: 1.0 mL/min.
measurement time: 40 min
analysis temperature: 25° C.
retention time: ethyl (2,6-difluorebenzyl)-[4-dimethylaminomethyl-3-(6-methoxypyridazin-3-yl-carbamoyl)-5-(4-nitrophenyl)thiophen-2-yl]carbamate (10.5 min), 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione (2.9 min)

Example 14 (Production of 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (in the Present Specification, to Also be Referred to as RS-2 (Related Substance 2)).)

To 1-(2,6-difluorobenzyl)-5-dimethylaminomethyl-3-(6-methoxypyridazin-3-yl)-6-(4-nitrophenyl)thieno[2,3-d]pyrimidine-2,4(1H,3H)-dione hydrochloride (9.0 g, 14.59 mmol) were added methanol (72 mL) and conc. hydrochloric acid (1.22 g, 11.67 mmol, 0.8 eq). 10% Pd—C NX type (0.9 g, containing 50% water) was added thereto under nitrogen atmosphere, and the mixture was stirred at 25±5° C. for 4 hr under hydrogen pressure of 0.2±0.1 MPa. The pH of the reaction mixture was adjusted to 6.5±0.5 with triethylamine at 25±5° C. Activated carbon (Shirasagi A, 0.45 g) was added thereto, and the mixture was stirred for 20-60 min. The activated carbon and catalyst were filtered off, and washed with methanol (18 mL). The filtrate was warmed to 40±5° C., and the pH of the mixture was adjusted to 8.0-8.5 with triethylamine. The mixture was aged with stirring at 40±5° C. for about 30 min, cooled to 5±5° C., and aged with stirring for 1 hr. The crystals were collected by filtration, washed twice with methanol (18 mL), and dried at 45±5° C. under reduced pressure until the weight became constant to give an almost white crystal of 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (6.93 g, yield: 86.3%, HPLC area percent: 99.5%).
<HPLC Condition>
detector: ultraviolet absorptiometer (measurement wavelength 254 nm)
column: YMC ODS-A A-302, 4.6 mm i.d.×150 mm
mobile phase: 0.05M $KH_2PO_4$ (pH7.0 by 10% KOH)/$CH_3CN$=55/45 (v/v)
flow rate: 1.0 mL/min.
measurement time: 30 min
analysis temperature: 25° C.
retention time: 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (4.8 min), 1-(2,6-difluorobenzyl)-5-dimethylaminomethyl-3-(6- methoxypyridazin-3-yl)-6-(4-nitrophenyl)thieno[2,3-d]
pyrimidine-2,4(1H,3H)-dione (16 min)

Example 15 (Production of a Crystal of a Tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea)

Acetonitrile (60 mL) and 1,1'-carbonyldiimidazole (CDI, 10.01 g, 61.75 mmol, 1.7 eq) were charged into a reactor, and the mixture was stirred. Triethylamine (3.12 g, 30.88 mmol, 0.85 eq) was added thereto with stirring, and the mixture was cooled to internal temperature of 10±5° C. Methoxyamine hydrochloride (5.79 g, 69.38 mmol, 1.91 eq) was added thereto with stirring in some portions at internal temperature of 30° C. or less, and the container used for the reagent was washed with acetonitrile (10 mL). The mixture was stirred at internal temperature of 25±5° C., and after confirming the dissolution of the mixture, the solution was stirred for additional 10 min or more. 6-(4-Aminophenyl)-1-(2,6-difluorobenzyl)-5-dimethylaminomethyl-3-(6-methoxypyridazin-3-yl)thieno[2,3-d]pyrimidine-2,4(1H,3H)-dione (20.00 g, 36.33 mmol) was added thereto with stirring, and the container used for the reagent was washed with acetonitrile (10 mL). The reaction mixture was warmed to internal temperature of 50±5° C., and stirred at the same temperature for 1 hr to give a reaction mixture. Again, triethylamine (4.70 g, 46.50 mmol, 1.28 eq) was added thereto with stirring at internal temperature of 50±5° C. City water (80 mL) was added dropwise thereto at internal temperature of 40-55° C., and the mixture was stirred for 1 hr, and city water (200 mL) was added dropwise thereto at internal temperature of 40-55° C. The mixture was aged with stirring at internal temperature of 25±5° C. for 1 hr or more. The crystals were collected by filtration, washed with a mixed solvent of city water (32 mL) and acetonitrile (8 mL), and dried at 50±10° C. under reduced pressure to give crude crystals (21.92 g). The crude crystals (21.0 g) were suspended in tetrahydrofuran (100 mL), and water was added thereto so that the water content was 5% relative to the crude crystals. The mixture was warmed to internal temperature of 40±5° C., and stirred at the same temperature for about 1 hr. The mixture was cooled to internal temperature of 5±5° C., and stirred at the same temperature for 1 hr. The crystals were collected by filtration, washed with tetrahydrofuran (40 mL), and dried at external temperature 50±10° C. under reduced pressure to give a crystal of a tetrahydrofuran solvate of 1-{4-[1-(2,6-difluorobenzyl)-5-dimethylaminomethyl-3-(6-methoxypyridazin-3-yl)-2,4-dioxo-Jo 1,2,3,4-tetrahydrothieno[2,3-d]pyrimidin-6-yl]phenyl}-3-methoxyurea (22.56 g, yield 93.2%, HPLC area percent: 99.8%).

Example 16 (Production of a Crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea)

Dimethylsulfoxide (20 mL) and a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (11.16 g) were charged into a reactor, and the mixture was dissolved by warming to internal temperature of 35±5° C. After confirming the dissolution of the mixture, the mixture was filtered through a dust removal filter, and washed with dimethylsulfoxide (5 mL). Ethanol (55 mL) was added thereto at internal temperature of 355° C., and then seed crystals (10 mg) obtained in Reference Example 5 were added thereto, and the mixture was stirred at internal temperature of 35±5° C. for 17 hr. Ethanol (120 mL) was added dropwise thereto at internal temperature of 35±5° C., and the mixture was cooled to internal temperature of 15±5° C., and stirred at the same temperature for about 31 hr. The crystals were collected by filtration, washed with ethanol (20 mL, cooled to 155° ° C.), and dried at external temperature 50±10° C. under reduced pressure to give 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (9.04 g, yield 90.4%, HPLC area percent: 99.8%) as white crystals.

The HPLC measurement conditions in Example 15 and Example 16 is shown in the following.
<HPLC Condition>
detector: ultraviolet absorptiometer (measurement wavelength 230 nm)
column: Sunfire C18 S-3.5 µm, 4.6 mm i.d.×10 cm (manufactured by Waters)
mobile phase: (A) a mixed solvent of 0.05 mol/L phosphorate buffer solution (pH2.0)/acetonitrile (31:9 (volume ratio))

(B) a mixed solvent of 0.05 mol/L phosphorate buffer solution (pH2.0)/acetonitrile (12:13 (volume ratio))
Gradient Program (Linear)

TABLE 6

| Time (min) | A solution (%) | B solution (%) |
|---|---|---|
| 0 (injection) | 100 | 0 |
| 20 | 100 | 0 |
| 55 | 0 | 100 |
| 55.1 | 100 | 0 |
| 65 | 100 | 0 | flow rate: 1.0 mL/min.
measurement time: 60 min
analysis temperature: 40° C.
retention time: 6-(4-aminophenyl)-1-(2,6-difluorobenzyl)-5-dimethylaminomethyl-3-(6-methoxypyridazin-3-yl) thieno[2,3-d]pyrimidine-2,4(1H,3H)-dione (7.7 min), 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (14.5 min)

Reference Example 5 (Production of a seed crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea)

Dimethylsulfoxide (25 mL) and 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (10.00 g) were charged into a reactor, and the mixture was dissolved by warming to internal temperature of 35±5° C. After confirming the dissolution of the mixture, ethanol (35 mL) was added thereto at internal temperature of 35±5° C., and the mixture was stirred at internal temperature of 35±5° C. for 5 days. After confirming that the precipitated crystals showed a powder X-ray diffraction pattern identical to that shown as in FIG. 2, ethanol (140 mL) was added dropwise thereto at internal temperature of 35±5° C., and the mixture was cooled to internal temperature of 25±5° C., and stirred at the same temperature for 3 days. The crystals were collected by filtration, washed with ethanol (20 mL, cooled to 25±5° C.), and dried at external temperature 50±10° C. under reduced pressure to give a seed crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (8.24 g, yield 82.4%) as white crystals.

<HPLC Condition>
detector: ultraviolet absorptiometer (measurement wavelength 230 nm)
column: Sunfire C18 S-3.5 µm, 4.6 mm i.d.×10 cm (manufactured by Waters)
mobile phase: (A) a mixed solvent of 0.05 mol/L phosphorate buffer solution (pH2.0)/acetonitrile (31:9 (volume ratio))
  (B) a mixed solvent of 0.05 mol/L phosphorate buffer solution (pH2.0)/acetonitrile (12:13 (volume ratio))
Gradient Program (Linear)

TABLE 7

| Time (min) | A solution (%) | B solution (%) |
|---|---|---|
| 0 (injection) | 100 | 0 |
| 20 | 100 | 0 |
| 55 | 0 | 100 |
| 55.1 | 100 | 0 |
| 65 | 100 | 0 | flow rate: 1.0 mL/min.
measurement time: 60 min
analysis temperature: 40° C.
retention time: 6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione (7.7 min), 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea (14.5 min)

INDUSTRIAL APPLICABILITY

According to the present invention, 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof with high quality can be more safely produced in high yield. In addition, a crystal of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof with high quality can be easily and efficiently produced.

Compounds (I) and (II) are useful as raw material compounds for producing 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof.

This application is based on patent application No. 217679/2012 filed in Japan, the contents of which are hereby incorporated by reference.

The invention claimed is:

1. A compound represented by the formula (II):

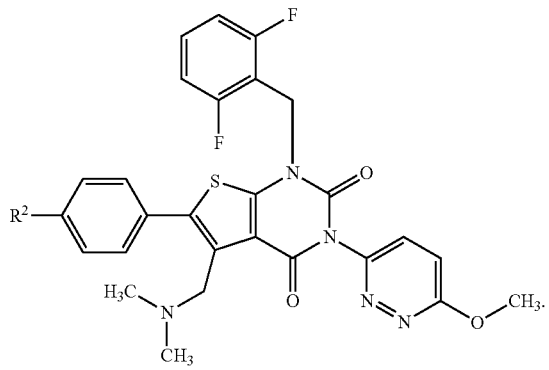

(II)

wherein $R^2$ is a nitro group or an amino group, or a salt thereof.

2. The compound of claim 1, wherein $R^2$ is a nitro group, or a salt thereof.

3. The compound of claim 1, wherein $R^2$ is an amino group, or a salt thereof.

* * * * *